US008933030B2

(12) United States Patent
Fretzen et al.

(10) Patent No.: US 8,933,030 B2
(45) Date of Patent: Jan. 13, 2015

(54) TREATMENTS FOR GASTROINTESTINAL DISORDERS

(75) Inventors: Angelika Fretzen, Somerville, MA (US); Hong Zhao, Lexington, MA (US); Marco Kessler, Danvers, MA (US)

(73) Assignee: Ironwwod Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 13/579,685

(22) PCT Filed: Feb. 17, 2011

(86) PCT No.: PCT/US2011/025274
§ 371 (c)(1),
(2), (4) Date: Mar. 29, 2013

(87) PCT Pub. No.: WO2011/103311
PCT Pub. Date: Aug. 25, 2011

(65) Prior Publication Data
US 2013/0190238 A1 Jul. 25, 2013
US 2014/0073571 A9 Mar. 13, 2014

Related U.S. Application Data

(60) Provisional application No. 61/305,465, filed on Feb. 17, 2010.

(51) Int. Cl.
| | | |
|---|---|---|
| A61K 38/00 | (2006.01) | |
| A61P 1/04 | (2006.01) | |
| A61K 38/12 | (2006.01) | |
| A61K 38/04 | (2006.01) | |
| C07K 5/00 | (2006.01) | |
| C07K 7/00 | (2006.01) | |
| C07K 16/00 | (2006.01) | |
| C07K 17/00 | (2006.01) | |
| C07K 7/08 | (2006.01) | |
| A61K 38/10 | (2006.01) | |
| A61K 45/06 | (2006.01) | |

(52) U.S. Cl.
CPC . *C07K 7/08* (2013.01); *A61K 38/10* (2013.01); *A61K 45/06* (2013.01)
USPC .......................... 514/13.2; 514/21.1; 530/327

(58) Field of Classification Search
None
See application file for complete search history.

(56) References Cited

U.S. PATENT DOCUMENTS

| | | | |
|---|---|---|---|
| 4,544,568 A | 10/1985 | Heyland et al. | |
| 4,806,524 A | 2/1989 | Kawaguchi et al. | |
| 4,992,419 A | 2/1991 | Woog et al. | |
| 5,221,495 A | 6/1993 | Cao | |
| 5,451,410 A | 9/1995 | Milstein et al. | |
| 5,593,696 A | 1/1997 | McNally et al. | |
| 5,654,278 A | 8/1997 | Sorensen | |
| 5,904,935 A | 5/1999 | Eckenhoff et al. | |
| 6,068,850 A | 5/2000 | Stevenson et al. | |
| 6,124,261 A | 9/2000 | Stevenson et al. | |
| 6,541,606 B2 | 4/2003 | Margolin et al. | |
| 6,734,162 B2 | 5/2004 | Van Antwerp et al. | |
| 6,828,303 B2 | 12/2004 | Kim et al. | |
| 6,979,437 B2 | 12/2005 | Bartus et al. | |
| 6,995,200 B2 | 2/2006 | Krohnke | |
| 7,056,942 B2 | 6/2006 | Hildesheim et al. | |
| 7,141,254 B2 | 11/2006 | Bhaskaran et al. | |
| 7,304,036 B2 | 12/2007 | Currie et al. | |
| 7,351,798 B2 | 4/2008 | Margolin et al. | |
| 7,371,727 B2 | 5/2008 | Currie et al. | |
| 7,494,979 B2 | 2/2009 | Currie et al. | |
| 7,704,947 B2 | 4/2010 | Currie et al. | |
| 7,745,409 B2 | 6/2010 | Currie et al. | |
| 7,767,644 B2 | 8/2010 | Schumann et al. | |
| 7,772,188 B2 | 8/2010 | Currie et al. | |
| 7,910,546 B2 | 3/2011 | Currie et al. | |
| 8,080,526 B2 | 12/2011 | Currie et al. | |
| 8,101,579 B2 | 1/2012 | Currie et al. | |
| 8,110,553 B2 | 2/2012 | Currie et al. | |
| 2003/0003563 A1 | 1/2003 | Vinkemeier et al. | |
| 2003/0069182 A1 | 4/2003 | Rinella | |
| 2003/0073628 A1 | 4/2003 | Shailubhai et al. | |
| 2003/0104996 A1 | 6/2003 | Li et al. | |

(Continued)

FOREIGN PATENT DOCUMENTS

| | | |
|---|---|---|
| JP | 64-009938 | 1/1989 |
| JP | 2003-201256 | 7/2003 |

(Continued)

OTHER PUBLICATIONS

Heck et al "Modification and Inhibition of Vancomycin Group Antibiotics by Formaldehyde and Acetaldehyde" Chemistry a European Journal 7:910-916. Published Feb. 16, 2001.*
Moss, Alex "Peptides Notes" Downloaded from <www.alchemyst.co.uk/alchemystry/pdf/Organic/peptides.pdf>. Published 2003.*
Andresen et al "Linaclotide Acetate" Drugs of the Future 33:570-576. Published Jul. 2008.*
Oliyai and Stella "Prodrugs of peptides and proteins for improved formulation and delivery" Annual Reviews of Pharmacology and Toxicology 32:521-544. Published 1993.*

(Continued)

*Primary Examiner* — James H Alstrum Acevedo
*Assistant Examiner* — Zachary J Miknis
(74) *Attorney, Agent, or Firm* — Honigman Miller Schwartz and Cohn LLP; Kelly T. Murphy; Jonathan P. O'Brien

(57) ABSTRACT

The present invention features peptides, compositions, and related methods for treating gastrointestinal disorders and conditions, including but not limited to, irritable bowel syndrome (IBS), gastrointestinal motility disorders, functional gastrointestinal disorders, gastroesophageal reflux disease (GERD), duodenogastric reflux, Crohn's disease, ulcerative colitis, inflammatory bowel disease, functional heartburn, dyspepsia, visceral pain, gastroparesis, chronic intestinal pseudo-obstruction (or colonic pseudo-obstruction), disorders and conditions associated with constipation, and other conditions and disorders are described herein, using peptides and other agents that activate the guanylate cyclase C (GC-C) receptor.

20 Claims, 4 Drawing Sheets

(56) References Cited

U.S. PATENT DOCUMENTS

| | | |
|---|---|---|
| 2003/0175230 A1 | 9/2003 | Dubief |
| 2004/0265242 A1 | 12/2004 | Bartus et al. |
| 2004/0266989 A1 | 12/2004 | Currie et al. |
| 2005/0020811 A1 | 1/2005 | Currie et al. |
| 2005/0080009 A1 | 4/2005 | Metzner et al. |
| 2007/0122354 A1 | 5/2007 | Hastedt et al. |
| 2007/0154406 A1 | 7/2007 | Moon et al. |
| 2007/0202165 A1 | 8/2007 | Heuer et al. |
| 2009/0062207 A1* | 3/2009 | Currie et al. ............ 514/14 |
| 2009/0110729 A1 | 4/2009 | Giovannone et al. |
| 2009/0253634 A1 | 10/2009 | Currie et al. |
| 2009/0305993 A1 | 12/2009 | Currie |
| 2010/0048489 A1* | 2/2010 | Fretzen et al. ............ 514/14 |
| 2010/0221329 A1 | 9/2010 | Shailubhai et al. |
| 2012/0009225 A1 | 1/2012 | Fretzen et al. |
| 2012/0039949 A1 | 2/2012 | Fretzen et al. |
| 2012/0213846 A1 | 8/2012 | Fretzen et al. |
| 2013/0012454 A1* | 1/2013 | Mo et al. ............ 514/21.1 |
| 2013/0190239 A1 | 7/2013 | FRETZEN et al. |
| 2013/0273169 A1 | 10/2013 | Fretzen et al. |

FOREIGN PATENT DOCUMENTS

| | | |
|---|---|---|
| WO | WO9012029 | 10/1990 |
| WO | WO9104743 | 4/1991 |
| WO | WO9703692 | 2/1997 |
| WO | WO9704796 | 2/1997 |
| WO | WO9800152 | 1/1998 |
| WO | WO9800157 | 1/1998 |
| WO | WO0004880 | 2/2000 |
| WO | WO0032172 | 6/2000 |
| WO | WO0226248 | 4/2002 |
| WO | WO02078683 | 10/2002 |
| WO | WO03014304 | 2/2003 |
| WO | WO03055511 | 7/2003 |
| WO | WO02062369 | 8/2003 |
| WO | WO2004052343 | 6/2004 |
| WO | WO2004069165 | 8/2004 |
| WO | WO2004108152 | 12/2004 |
| WO | WO2005014025 | 2/2005 |
| WO | WO2005042029 | 5/2005 |
| WO | WO2005087797 | 9/2005 |
| WO | WO2007022531 | 2/2007 |
| WO | WO2007044375 | 4/2007 |
| WO | WO2008006125 | 1/2008 |
| WO | WO2008021133 | 2/2008 |
| WO | WO2008027854 | 3/2008 |
| WO | WO2008078189 | 7/2008 |
| WO | WO2008106429 | 9/2008 |
| WO | WO2008151257 | 12/2008 |
| WO | WO2010019266 | 2/2010 |
| WO | WO2010065751 | 6/2010 |
| WO | WO2011019819 | 2/2011 |
| WO | WO2011056850 | 3/2013 |

OTHER PUBLICATIONS

Ahmed, Hashim and Shah, Navnit., "Formulations of Low Dose Medicines—Theory and Practice." American Pharmaceutical Review, 3(3): 1-4, 2000.

Andresen et al., "Effect of 5 days of linaclotide on transit and bowel function in females with constipation-predominant irritable bowel syndrome." Gastroenterology, 133(3):761-768, 2007.

Aventis Pharmaceuticals, Inc. (2002). DDAVP (desmopressin acetate) tablet, [Product Label]. Bridgewater, NJ 08807, USA.

Bedu-Addo, F. et al., "Preformulation Development of Recombinant Pegylated Staphylokinase SY161 Using Statistical Design." AAPS PharmSci (http://www.aapspharmsci.org), 4(4) article 19, 1-11, 2002.

Bedu-Addo, F.K. et al., "Use of Biophysical Characterization in Preformulation Development of a Heavy-Chain Fragment of Botulinum Serotype B: Evaluation of Suitable Purification Process Conditions." Pharmceutical Research, 21(8): 1353-1361, 2004.

Camilleri, "Management of the Irritable Bowel Syndrome" Gastroenterology, 120:652-668, 2001.

Capasso et al., "Deamidation via Cyclic Imide of Asparaginyl Peptides: Dependence on Salts, Buffers and Organic Solvents." Peptide Research, 4(4): 234-238, 1991.

Carpenter et al., "Rational Design of Stable Lyophilized Protein Formulations: Some Practical Advice." Pharmaceutical Research, 14(8): 969-975, 1997.

Carson et al.,"Effect of Linaclotide on Quality of Life in Adults With Chronic Constipation: Results From 2 Randomized, Double-Blind, Placebo-Controlled Phase III Trials." Gastroenterology, 139(1):E19, 2010.

Chourasia, M.K. and Jain, S.K., "Pharmaceutical approaches to colon targeted drug delivery systems." J Pharm Pharmaceut Sci (www.ualberta.ca/-csps), 6(1): 33-66, 2003.

Cleland et al., "The Development of Stable Protein Formulations: A Close Look at Protein Aggregation, Deamidation, and Oxidation." Critical Reviews in Therapeutic Drug Carrier Systems, 10(4): 307-377, 1993.

Constantino, H.R, et al., "Moisture-Induced Aggregation of Lyophilized Insulin". Pharmaceutical Research, 11(1): 21-29, 1994.

Cook et al., "Chronic constipation: Overview and Challenges." Neurogastroenterology and Motility, 21(supp2): 1-8, 2009.

Dulbecco et al., "Plaque formation and isolation of pure liner with poliomyelitis viruses." Journal of Experimental Medicine, 99(2): 167-182, 1954.

Elan Pharmaceuticals, Inc. (2004). Prialt (ziconotide) injection, solution, [Product Label]. San Diego, CA 92121, USA.

Fix, J.A., "Oral Controlled Release Technology for Peptides: Status and Future Prospects." Pharmaceutical Research, 13(12): 1760-1764, 1996.

Forest, "Phase III randomized double-blind placebo-controlled trial of linaclotide administered to patients with chronic constipation." 2008. Retrieved from <<http:www.clinicaltrials.gov>> identifier NCT00765882 on Dec. 9, 2010.

Fu et al., "Protein Stability in Controlled-Release Systems." Nature Biotechnology, 18: 24-25, 2000.

Grenha et al., "Chitosan nanoparticles are compatible with respiratory epithelial cells in vitro." European Journal of Pharmaceutical Sciences, 31: 73-84, 2007.

Harris et al., "Drug evaluation: Linaclotide, a new direction in the treatment of irritable bowel syndrome and chronic constipation." Current Opinion in Molecular Therapeutics, 9(4):403-410, 2007.

"International Nonproprietary Names for Pharmaceutical Substances (INN)." WHO Drug Information, 21(3): 247-264, 2007.

Johnston et al., "Pilot study on the effect of linaclotide in patients with chronic constipation." Am. J. Gastroenterol., 104(1):125-132, 2009.

Kirby, "Oil-Based Formulations for Oral Delivery of Therapeutic Peptides." Journal of Liposome Research, 10(4): 391-407, 2000.

Langer, R. "Drug delivery and targeting", Nature; 392 (Supp): 5-10, 1998.

Lavins et al, "418 Effect of Linaclotide on Quality of Life in Adults with Chronic Constipation: Results from a Phase 2B Study." Gastroenterology, 136(5): A71, 2009.

Lechuga-Ballesteros et al., "Trileucine Improves Aerosol Performance and Stability of Spray-dried Powders for Inhalation." Journal of Pharmaceutical Sciences, 97(1): 287-302, 2008.

Lembo et al., "Linaclotide significantly improved bowel habits and relieved abdominal symptoms in adults with chronic constipation: Data from a large 4-week, randomized, double-blind, placebo-controlled study." Gastroenterology, 135 (1):295, 2008.

Lembo et al., "157 Effect of Linaclotide on IBS-C Symptoms in the First Week of Treatment: Results from a Phase 2B Study." Gastroenterology, 136(5):A30, 2009.

Mehta, N.M., "Oral Delivery and Recombinant Production of Peptide Hormones. Part I: Making Oral Delivery Possible: Enteric-coated capsules or tablets with additional excipients enable intestinal delivery." Bio-Pharm International (www.biopharm-mag.com), Jun. 1-6, 2004.

Mehta, N.M., "Oral Delivery and Recombinant Production of Peptide Hormones. Part II: Recombinant Production of Therapeutic Peptides." Bio-Pharm International (www.biopharm-mag.com), Jun. 7-9, 2004.

(56) References Cited

OTHER PUBLICATIONS

Microbia, Forest, "Microbia and Forest Laboratories Announce Preliminary Results of Linaclotide Phase 2B Studies." Communications of Microbia, pp. 1-4, 2008.
Oliyai et al., "Chemical Pathways of Peptide Degradation. VII. Solid State Chemical Instability of an Aspartyl Residue in a Model Hexapeptide." Pharmaceutical Research, 11(6): 901-908, 1994.
Oliyai et al., "Solid State Chemical Instability of an Asparaginyl Residue in a Model Hexapeptide." Journal of Pharmaceutical Science & Technology, 48(3): 167-173, 1994.
Patel, K. and Borchardt, R.T., "Chemical Pathways of Peptide Degradation. III. Effect of Primary Sequence on the Pathways of Deamidation of Asparaginyl Residues in Hexapeptides." Pharmaceutical Research, 7(8): 787-793, 1990.
Patel, K. and Borchardt, R.T., "Deamidation of Asparaginyl Residues in Proteins: A Potential Pathway for Chemical Degradation of Proteins in Lyophilized Dosage Forms." Journal of Parenteral Science & Technology, 44(6): 300-301, 1990.
Reporter'S Guide to Irritable Bowel Syndrome, retrieved from <<http:www.aboutibs.org/pdfs/ReportersGuideIBS.pdf>> on Nov. 28, 2012, total of 18 pages where the main text is numbered as pp. 1-14.
Sejourne, F. et al., "Development of a Novel Bioactive Formulation of Vasoactive Intestinal Peptide in Sterically Stabilized Liposomes." Pharmaceutical Research, 14(3): 362-365, 1997.
Shailubhai et al., "Uroguanylin treatment suppresses polyp formation in the Apc(Min/+) mouse and induces apoptosis in human colon adenocarcinoma cells via cyclic GMP." Cancer Res., 60:5151-5157, 2000.
Vippagunta et al., "Crystalline solids." Advanced Drug Delivery Reviews, 48:3-26, 2001.
Camilleri et al., "Challenges to the Therapeutic Pipeline for Irritable Bowel Syndrome: End Points and Regulatory Hurdles." Gastroenterology. 135:1877-1891, 2008.

\* cited by examiner

TREATMENTS FOR GASTROINTESTINAL DISORDERS

PRIORITY CLAIM

This application is a national phase application of PCT/US2011/025274, filed on Feb. 17, 2011, which claims priority to U.S. Provisional Patent Application Ser. No. 61/305,465, filed Feb. 17, 2010. The entire contents of the aforementioned applications are incorporated herein by reference.

FIELD OF THE INVENTION

This invention relates to peptides, compositions and methods for treating gastrointestinal disorders.

SEQUENCE LISTING

This application incorporates by reference in its entirety the Sequence Listing entitled "IW087_seq_ST25.txt" (527 bytes), which was created Feb. 17, 2011 and filed electronically herewith.

BACKGROUND

Gastrointestinal disorders (GI) include irritable bowel syndrome (IBS) which is a common chronic disorder of the intestine that affects 20 to 60 million individuals in the US alone (Lehman Brothers, Global Healthcare-Irritable bowel syndrome industry update, September 1999). IBS is the most common disorder diagnosed by gastroenterologists and accounts for 12% of visits to primary care physicians (Camilleri 2001, Gastroenterology 120:652-668). In the US, the economic impact of IBS is estimated at $25 billion annually, through direct costs of health care use and indirect costs of absenteeism from work (Talley 1995, Gastroenterology 109:1736-1741). Patients with IBS have three times more absenteeism from work and report a reduced quality of life. There is a tremendous unmet medical need for patients suffering for IBS since few prescription options exist to treat IBS.

Patients with IBS suffer from abdominal pain and a disturbed bowel pattern. Three subgroups of IBS patients have been defined based on the predominant bowel habit: constipation-predominant irritable bowel syndrome (c-IBS), diarrhea-predominant irritable bowel syndrome (d-IBS) or alternating between the two irritable bowel syndromes (a-IBS). Estimates of individuals who suffer from c-IBS range from 20-50% of the IBS patients with 30% frequently cited. In contrast to the other two subgroups that have a similar gender ratio, c-IBS is more common in women (ratio of 3:1) (Talley et al. 1995, Am J Epidemiol 142:76-83).

The definition and diagnostic criteria for IBS have been formalized in the "Rome Criteria" (Drossman et al. 1999, Gut 45: Suppl II: 1-81), which are well accepted in clinical practice. Recently, there has been increasing evidence for a role of inflammation in etiology of IBS. Reports indicate that subsets of IBS patients have small but significant increases in colonic inflammatory and mast cells, increased inducible nitric oxide (NO) and synthase (iNOS) and altered expression of inflammatory cytokines (reviewed by Talley 2000, Medscape Coverage of DDW week).

Gastrointestinal disorders can also include constipation wherein as many as 34 million Americans suffer from symptoms associated with chronic constipation (CC) and 8.5 million patients have sought treatment. Patients with CC often experience hard and lumpy stools, straining during defecation, a sensation of incomplete evacuation, and fewer than three bowel movements per week. The discomfort and bloating of CC significantly affects patients' quality of life by impairing their ability to work and participate in typical daily activities.

Half of CC patients are not satisfied with currently available treatments for CC. Thus, there remains a need for new compounds and methods of treating CC.

U.S. Pat. Nos. 7,304,036 and 7,371,727 disclose peptides that act as agonists of the guanylate cyclase C (GC-C) receptor for the treatment of gastrointestinal disorders. One particular peptide disclosed is linaclotide, which consists of the following amino acid sequence: Cys Cys Glu Tyr Cys Cys Asn Pro Ala Cys Thr Gly Cys Tyr (SEQ ID NO:1). These patents also disclose methods for preparing linaclotide and related peptides.

Linaclotide has the amino acid structure of:

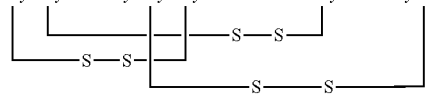

Linaclotide is orally administered and currently in clinical trials for treatment of irritable bowel syndrome with constipation (IBS-c) and chronic constipation (CC), has numerous effects on GI physiology including: (1) reduced visceral pain, (2) reduced bloating, and (3) increased GI transit, which can lead to increased stool frequency and improved stool consistency. Orally administered linaclotide acts locally by activating GC-C at the luminal surface; there are no detectable levels of linaclotide seen systemically after oral administration at therapeutic dose levels. Thus, the results from clinical trials of linaclotide, as well as preclinical studies that have been done with linaclotide and related peptides, suggest that GC-C peptide agonists may be used therapeutically.

The contents of the U.S. Pat. Nos. 7,304,036 and 7,371,727 are incorporated herein by reference in their entirety.

The present invention feature peptides which may be modified at their amine groups into imidazolidinone derivatives and/or modified at their carboxyl groups into alkyl esters that are capable of activating and/or binding the guanylate cyclase-C (GC-C) receptors at different affinities. GC-C is a key regulator in mammals of intestinal function, although low levels of GC-C have been detected in other tissues. GC-C responds to the endogenous hormones, guanylin and uroguanylin, and to enteric bacterial peptides from the heat stable enterotoxin family (ST peptide). When agonists bind to GC-C, there is an elevation of the second messenger, cyclic GMP (c-GMP), and an increase in chloride and bicarbonate secretion, resulting in an increase in intestinal fluid secretion. In some examples of the present invention, the peptides described herein may produce increased elevation of c-GMP levels and provide a therapeutic option for treating gastrointestinal disorders.

SUMMARY

The present invention features peptides, compositions, and related methods for treating gastrointestinal disorders and conditions, including but not limited to, irritable bowel syndrome (IBS) gastrointestinal motility disorders, constipation, functional gastrointestinal disorders, gastroesophageal reflux disease (GERD), duodenogastric reflux, Crohn's disease, ulcerative colitis, inflammatory bowel disease, functional heartburn, dyspepsia, visceral pain, gastroparesis, chronic intestinal pseudo-obstruction (or colonic pseudo-obstruction), and other conditions and disorders described herein using peptides and compositions that activate the guanylate cyclase C (GC-C) receptor.

One aspect of the present invention provides a peptide or a pharmaceutically acceptable salt thereof, wherein the peptide comprises the amino acid sequence Cys Cys Glu Tyr Cys Cys Asn Pro Ala Cys Thr Gly Cys Tyr (SEQ ID NO:1), wherein at least one carboxyl group of the peptide is an alkyl ester having the formula (—COOR) in which R is a $C_{1-6}$ alkyl.

In one embodiment, the peptide comprises the amino acid structure of:

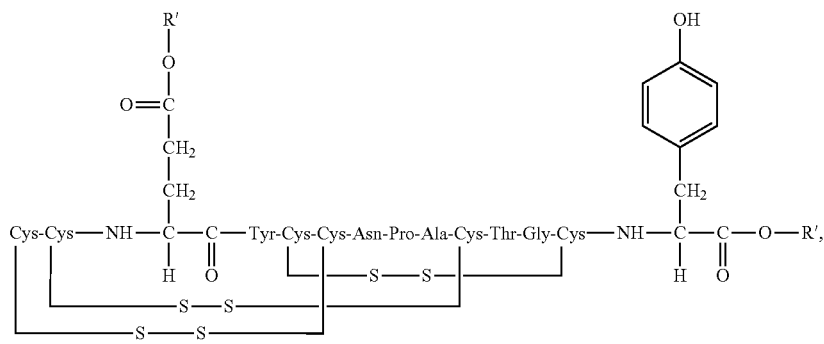

or a pharmaceutically acceptable salt thereof, wherein R' is H or a $C_{1-6}$ alkyl, and at least one R' is $C_{1-6}$ alkyl.

A second aspect of the present invention provides a peptide that comprises the amino acid structure of:

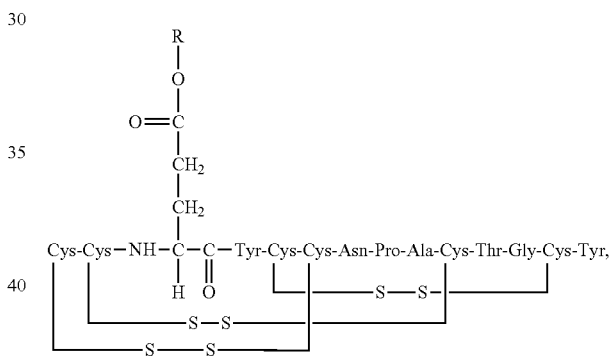

or a pharmaceutically acceptable salt thereof, wherein R is a $C_{1-6}$ alkyl; or a peptide that comprises the amino acid structure of:

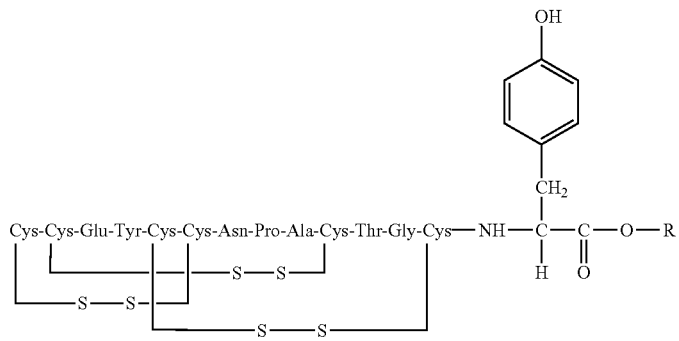

or a pharmaceutically acceptable salt thereof, wherein R is $C_{1-6}$ alkyl.

A third aspect of the present invention provides a peptide or pharmaceutically acceptable salt thereof, wherein the peptide comprises the amino acid structure of:

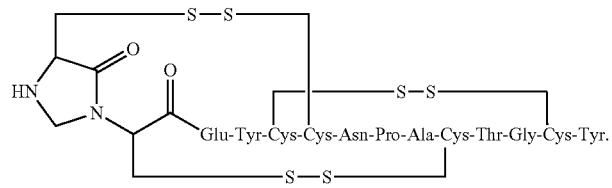

A fourth aspect of the present invention provides a pharmaceutical composition comprising a peptide of the present invention.

A fifth aspect of the present invention provides a method for treating a gastrointestinal disorder, which includes administering a pharmaceutical composition according to the present invention.

The details of one or more embodiments of the invention are set forth in the accompanying description.

Figure 1:
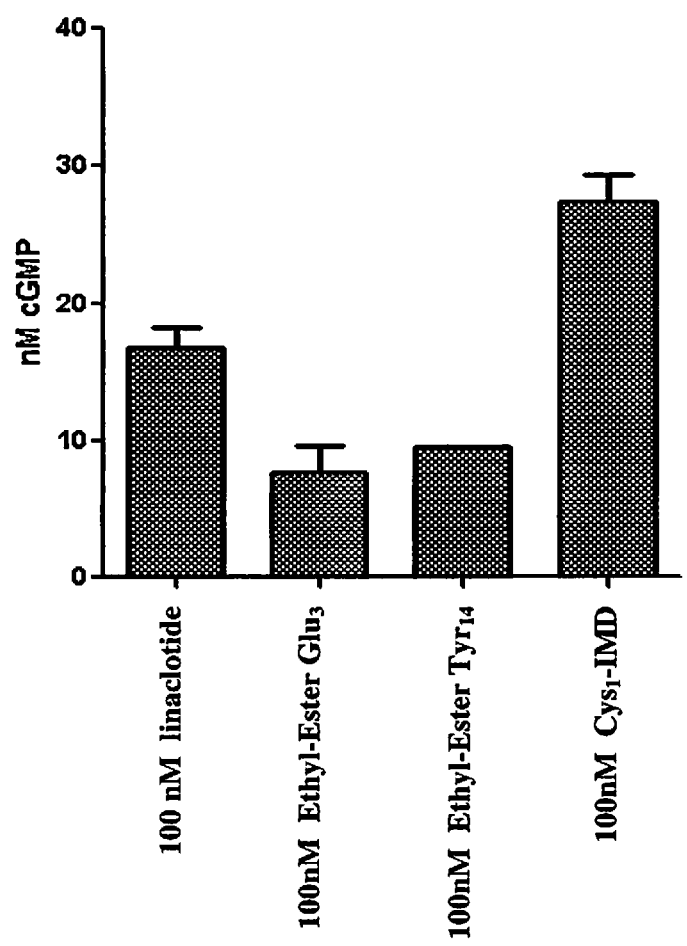
FIG. 1 shows the dose response of exemplary peptides of the present invention in a T84 cell c-GMP assay.

The figures are provided by way of example and are not intended to limit the scope of the present invention.

DETAILED DESCRIPTION

Guanylate cyclase C (GC-C) is a transmembrane receptor that is located on the apical surface of epithelial cells in the stomach and intestine. The receptor has an extracellular ligand-binding domain, a single transmembrane region and a C-terminal guanylyl cyclase domain. When a ligand binds to the extracellular domain of GC-C, the intracellular catalytic domain catalyzes the production of cGMP from GTP. In vivo, this increase in intracellular cGMP initiates a cascade of events that leads to increased secretion of chloride and bicarbonate into the intestinal lumen, increased luminal pH, decreased luminal sodium absorption, increased fluid secretion, and acceleration of intestinal transit. cGMP is secreted bidirectionally from the epithelium into the mucosa and lumen. The peptides and compositions of the present invention bind to the intestinal GC-C receptor which is a regulator of fluid and electrolyte balance in the intestine.

In some circumstances it can be desirable to treat patients with a variant or modified peptide that binds to and activates intestinal GC-C receptors, but is less active or more active than the non-variant form of a peptide. Reduced activity can arise from reduced affinity for the receptor or a reduced ability to activate the receptor once bound or reduced stability of the peptide. Increased activity can arise from increased affinity for the receptor or an increased ability to activate the receptor once bound or increased stability of the peptide.

Description of Exemplary Peptides:

In various embodiments, a peptide may be modified wherein at least one carboxyl group of the amino acid residue of the peptide is modified to an alkyl ester. This modification may be produced, for example, by treating a carboxylic acid with an alcohol in the presence of a dehydrating agent wherein the dehydrating agent can include but is not limited to a strong acid such as sulfuric acid. Other methods of producing alkyl esters from carboxyl groups are readily known in those skilled in the arts and are incorporated herein.

As used herein, a carboxyl group has the formula: (—COOH).

As used herein, the term "alkyl", refers to a saturated linear or branched-chain monovalent hydrocarbon radical.

As used herein, a group is terminal or terminus when the group is present at the end of the amino acid sequence.

As used herein, an amine group on a peptide has the formula:

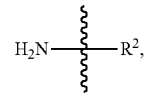

wherein $R^2$ is the rest of the peptide.

As used herein, an imine group on a peptide has the formula:

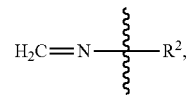

wherein $R^2$ is the rest of the peptide.

In some embodiments, the carboxylic acid of the side chain of a glutamate amino acid in a peptide sequence is modified into an alkyl ester.

In further embodiments, the carboxylic acid on the side chain of a glutamate amino acid a peptide sequence is modified into an ethyl ester.

In other embodiments, the C-terminus carboxylic acid of a tyrosine amino acid in a peptide sequence is modified into an alkyl ester.

In further embodiments, the C-terminus carboxylic acid of a tyrosine amino acid of a peptide sequence is modified into an ethyl ester.

In several embodiments, the present invention provides a peptide or a pharmaceutically acceptable salt thereof, wherein the peptide comprises the amino acid sequence Cys Cys Glu Tyr Cys Cys Asn Pro Ala Cys Thr Gly Cys Tyr (SEQ ID NO:1), wherein at least one carboxyl group of the peptide is an alkyl ester having the formula (—COOR) in which R is a $C_{1-6}$ alkyl.

In several embodiments, the peptide comprises an amino acid structure of:

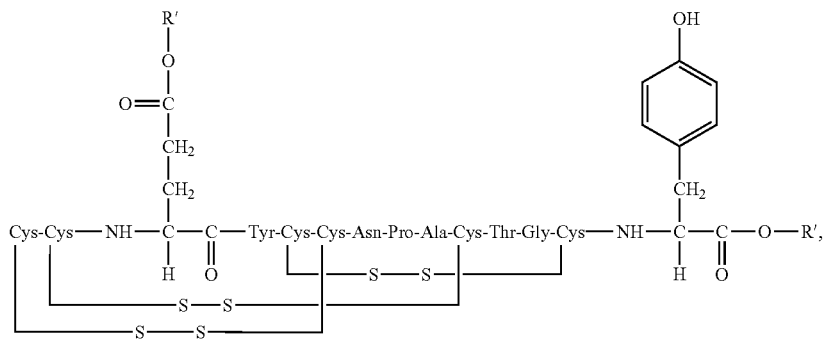

or a pharmaceutically acceptable salt thereof, wherein R' is H or a $C_{1-6}$ alkyl, and at least one R' is $C_{1-6}$ alkyl.

In some embodiments, the peptide or pharmaceutically acceptable salt thereof comprises a peptide having an amino acid structure of:

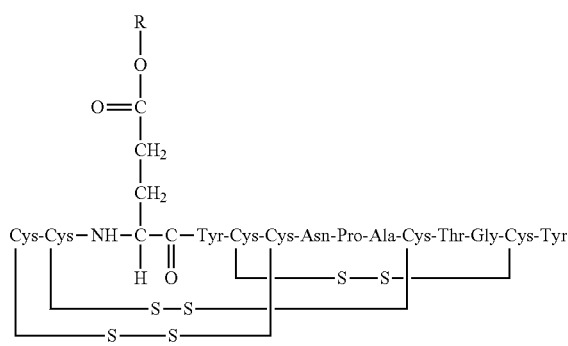

wherein R is a $C_{1-6}$ alkyl ("Glu$_3$-alkyl ester").

In other embodiments, R is a $C_{1-4}$ alkyl.

In further embodiments, R is methyl, ethyl, or propyl.

In some embodiments, the peptide or pharmaceutically acceptable salt thereof comprises an amino acid structure of ("Glu$_3$-ethyl ester"):

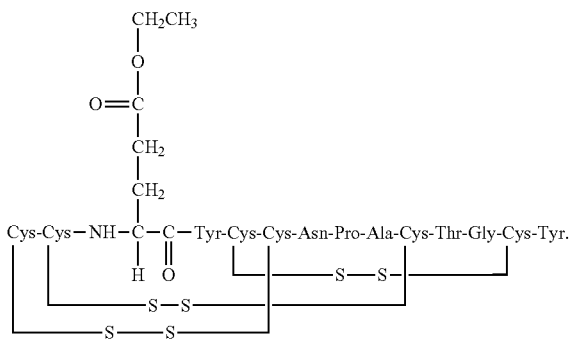

In some embodiments, the peptide or pharmaceutically acceptable salt thereof comprises an amino acid structure of:

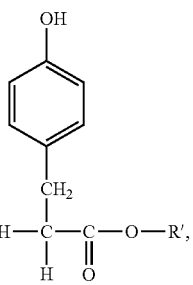

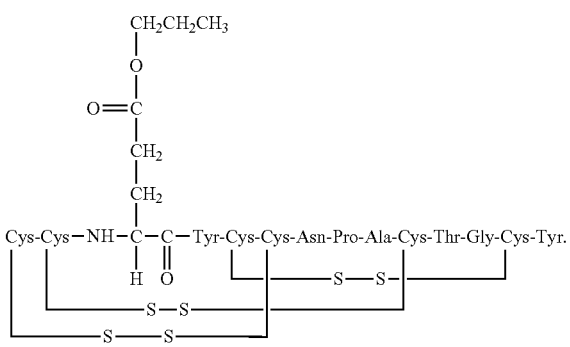

In some embodiments, the peptide or pharmaceutically acceptable salt thereof comprises an amino acid structure of:

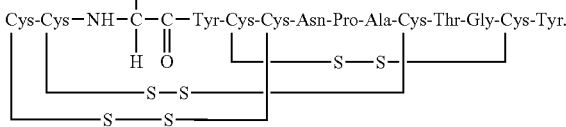

In some embodiments, the C-terminal tyrosine of the Glu$_3$-alkyl ester or pharmaceutically acceptable salt is absent.

In some embodiments, the peptide or pharmaceutically acceptable salt thereof comprises an amino acid structure of:

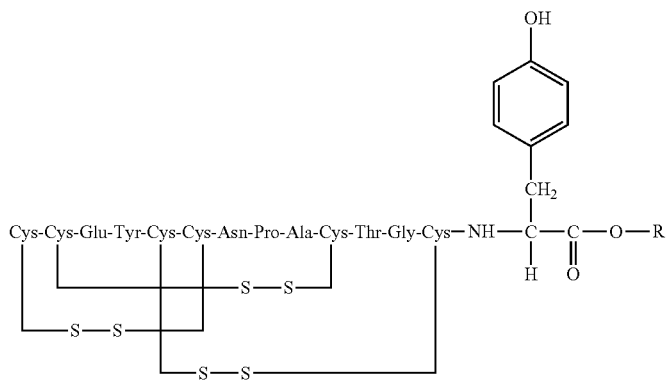

wherein R is $C_{1-6}$ alkyl.

In other embodiments, R is a $C_{1-4}$ alkyl.

In further embodiments, R is methyl, ethyl, or propyl.

In some embodiments, the peptide or pharmaceutically acceptable salt thereof comprises an amino acid structure of ("$Tyr_{14}$-ethyl ester"):

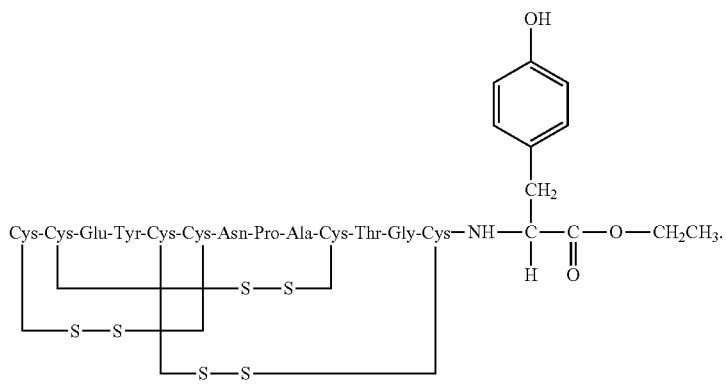

In some embodiments, the peptide or pharmaceutically acceptable salt thereof comprises an amino acid structure of:

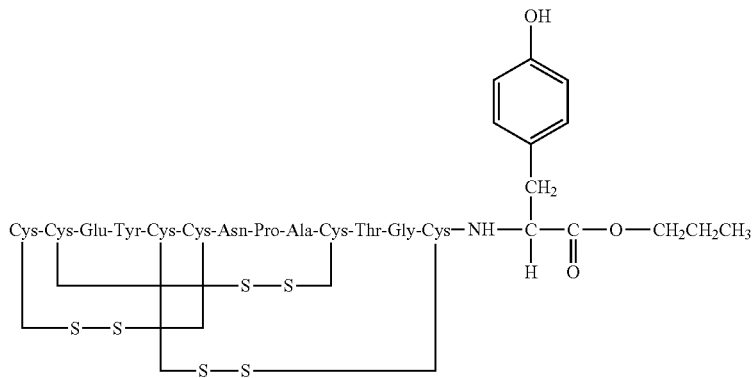

In some embodiments, the peptide or pharmaceutically acceptable salt thereof comprises an amino acid structure of:

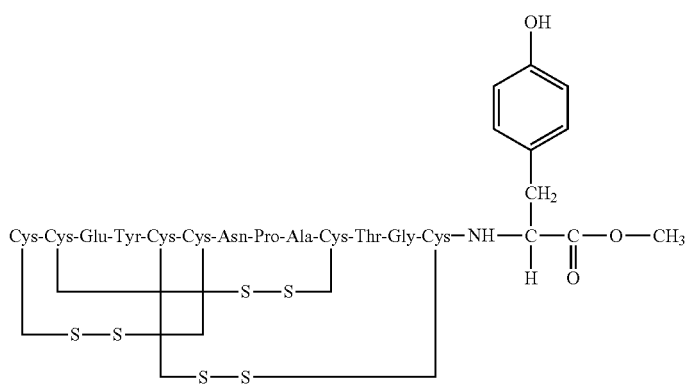

Without wishing to be bound by any theory, a peptide may be modified wherein at least one amine group of the amino acid residues of the peptide is modified into an imine. This modification may be produced, for example, by treating an amine group with a carbonyl, such as an aldehyde or ketone, in the presence of acid catalyst. Other methods of producing imines from amine groups are readily known to those skilled in the arts and are incorporated herein.

In some embodiments, the imine modification may be produced by a formaldehyde mediated reaction in the presence of acid catalyst.

In further embodiments, the imine carbon may be cross-linked to another amine group of the peptide.

In other embodiments, a peptide may be modified into an imine at the α-amine group of the N-terminal amino acid, wherein the imine carbon is cross-linked with an amine group of the second amino acid residue of the peptide forming a five membered ring.

In other embodiments, a peptide comprising the amino acid sequence Cys Cys Glu Tyr Cys Cys Asn Pro Ala Cys Thr Gly Cys Tyr (SEQ ID NO:1) may be modified with the addition of methylene at the α-amine group of the N-terminal Cys$_1$ which is cross-linked to the amine group of Cys$_2$ to form an imidazolidinone 5 membered ring at the N-terminus of the peptide ("Cys$_1$-IMD").

In one aspect, the invention provides novel GC-C peptide agonists useful for the treatment of gastrointestinal disorders.

In several embodiments, the present invention provides a peptide or a pharmaceutically acceptable salt thereof, wherein the peptide comprises the amino acid sequence Cys Cys Glu Tyr Cys Cys Asn Pro Ala Cys Thr Gly Cys Tyr (SEQ ID NO:1), wherein at least one amine group of the peptide is an imine having the formula

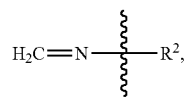

wherein R$^2$ is the rest of the peptide.

In some embodiments, the peptide or a pharmaceutically acceptable salt comprises a peptide wherein the N-terminal amine group of the peptide is an imine having the formula

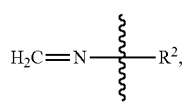

wherein R$^2$ is the rest of the peptide.

In further embodiments, the peptide or pharmaceutically acceptable salt thereof comprises an amino acid structure of:

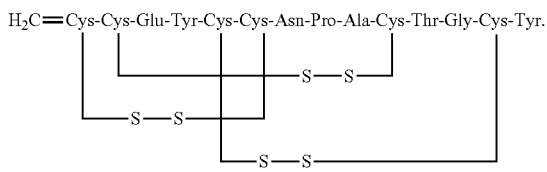

In several embodiments, the peptide or pharmaceutically acceptable salt thereof comprises an amino acid structure of:

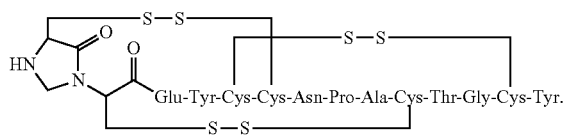

In some embodiments, the C-terminal tyrosine of the Cys$_1$-IMD peptide or pharmaceutically acceptable salt thereof is absent. In some embodiments, the Cys$_1$-IMD peptide or pharmaceutically acceptable salt thereof further comprises one or more peptide modifications, wherein at least one carboxyl group of the peptide is an alkyl ester having the formula (—COOR) in which R is a C$_{1-6}$ alkyl.

In several embodiments, the present invention provides a peptide or a pharmaceutically acceptable salt thereof, wherein the peptide consists of the amino acid sequence Cys Cys Glu Tyr Cys Cys Asn Pro Ala Cys Thr Gly Cys Tyr (SEQ ID NO:1), wherein at least one carboxyl group of the peptide is an alkyl ester having the formula (—COOR) in which R is a C$_{1-6}$ alkyl.

In several embodiments, the peptide consists of an amino acid structure of:

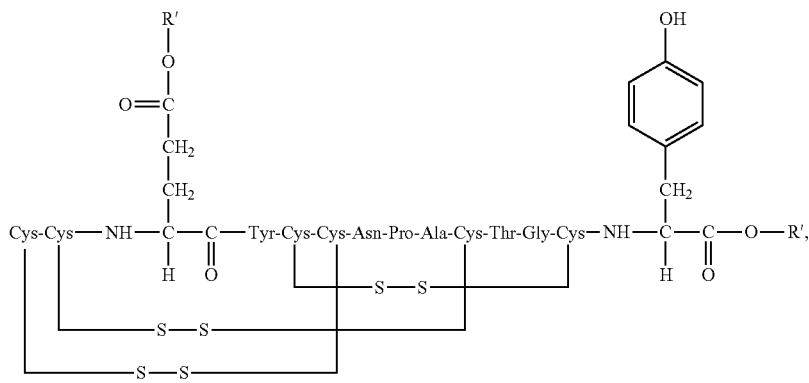

or a pharmaceutically acceptable salt thereof, wherein R' is H or a $C_{1-6}$ alkyl, and at least one R' is $C_{1-6}$ alkyl.

In some embodiments, the peptide or pharmaceutically acceptable salt thereof consists of an amino acid structure of:

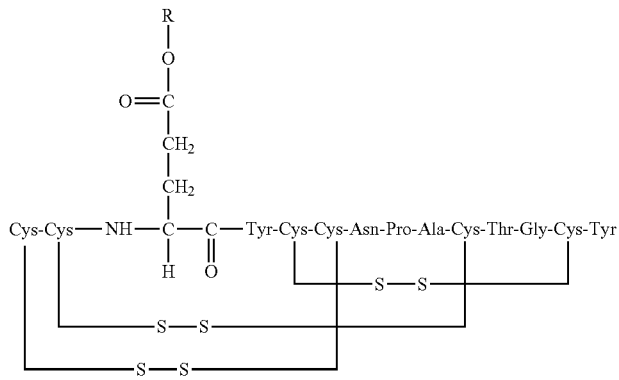

wherein R is a $C_{1-6}$ alkyl. In further embodiments, the C-terminal tyrosine is absent.

In other embodiments, R is a $C_{1-4}$ alkyl.

In further embodiments, R is methyl, ethyl, or propyl.

In some embodiments, the peptide or pharmaceutically acceptable salt thereof consists of a peptide having an amino acid structure of:

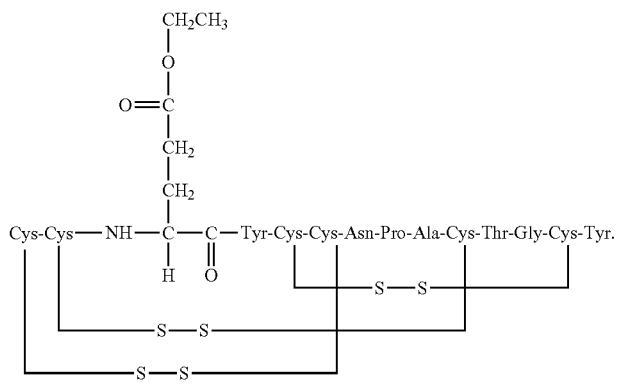

In some embodiments, the peptide or pharmaceutically acceptable salt thereof consists of a peptide having an amino acid structure of:

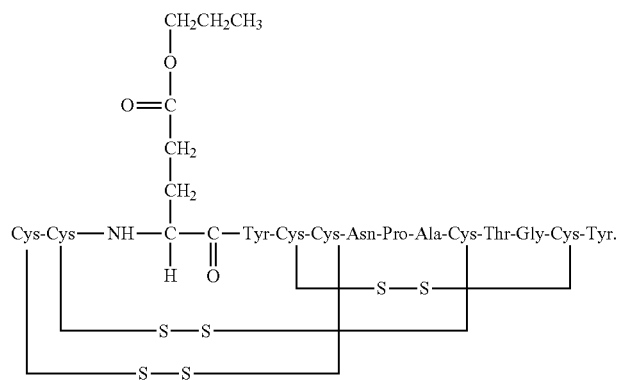

In some embodiments, the peptide or pharmaceutically acceptable salt thereof consists of a peptide having an amino acid structure of:

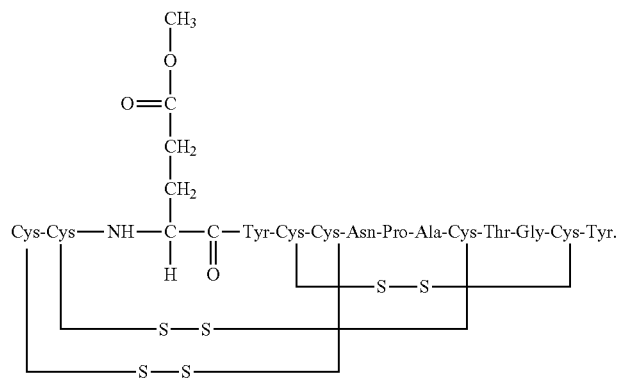

In some embodiments, the peptide or pharmaceutically acceptable salt thereof consists of a peptide having an amino acid structure of:

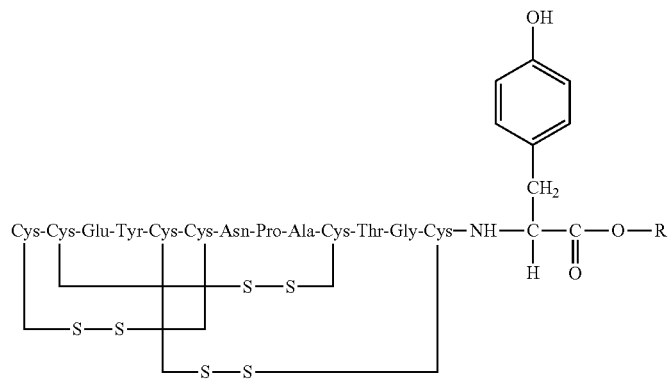

wherein R is $C_{1-6}$ alkyl.

In other embodiments, R is a $C_{1-4}$ alkyl.

In further embodiments, R is methyl, ethyl, or propyl.

In some embodiments, the peptide or pharmaceutically acceptable salt thereof consists of an amino acid structure of:

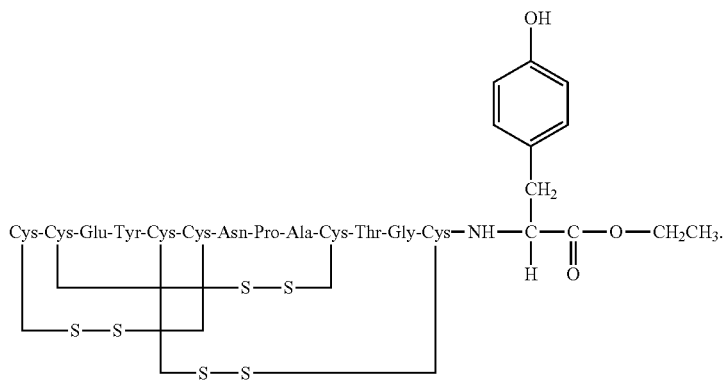

In some embodiments, the peptide or pharmaceutically acceptable salt thereof consists of an amino acid structure of:

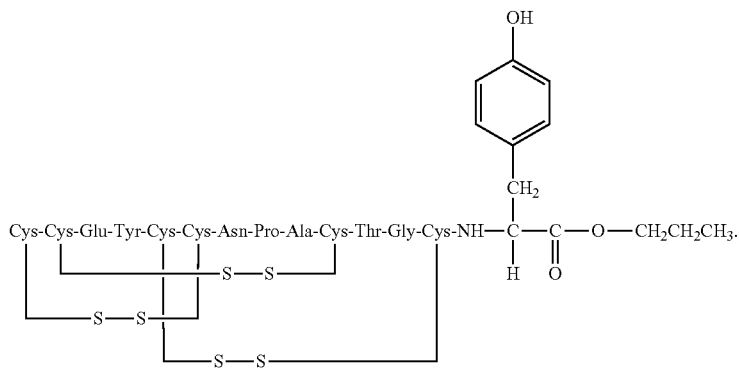

In some embodiments, the peptide or pharmaceutically acceptable salt thereof consists of an amino acid structure of:

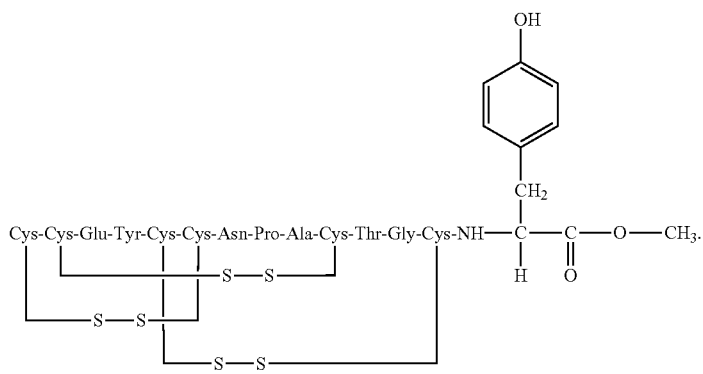

In several embodiments, the present invention provides a peptide or a pharmaceutically acceptable salt thereof, wherein the peptide consists of the amino acid sequence Cys Cys Glu Tyr Cys Cys Asn Pro Ala Cys Thr Gly Cys Tyr (SEQ ID NO:1), wherein at least one amine group of the peptide is an imine having the formula

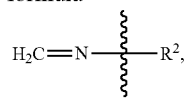

wherein $R^2$ is the rest of the peptide.

In some embodiments, the peptide or a pharmaceutically acceptable salt consists of a peptide wherein the N-terminal amine group of the peptide is an imine having the formula

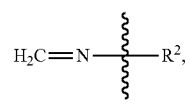

wherein $R^2$ is the rest of the peptide.

In further embodiments, the peptide or pharmaceutically acceptable salt thereof consists of an amino acid structure of:

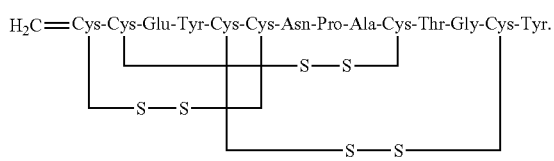

In some embodiments, the peptide or pharmaceutically acceptable salt thereof consists of an amino acid structure of:

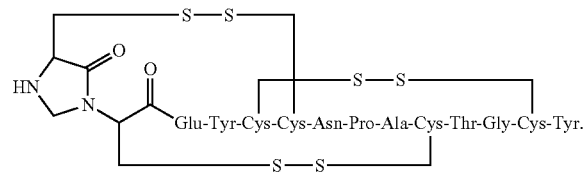

In some embodiments, the C-terminal tyrosine of the $Cys_1$-IMD peptide or pharmaceutically acceptable salt thereof is absent. In some embodiments, the $Cys_1$-IMD peptide or pharmaceutically acceptable salt thereof further comprises one or more peptide modifications, e.g., wherein at least one carboxyl group of the peptide is an alkyl ester having the formula (—COOR), wherein R is a $C_{1-6}$ alkyl.

In some embodiments, the peptide or pharmaceutically acceptable salt thereof activates the guanylate cyclase C receptor.

In other embodiments, the peptide or pharmaceutically acceptable salt thereof comprises 30 or fewer amino acids.

In further embodiments, the peptide or pharmaceutically acceptable salt thereof comprises 20 or fewer amino acids.

In other embodiments, the peptide or pharmaceutically acceptable salt thereof comprises a peptide wherein fewer than five amino acids precede the first Cys residue of the amino acid sequence.

In some embodiments, the peptide or pharmaceutically acceptable salt thereof is isolated.

In other embodiments, the peptide or pharmaceutically acceptable salt thereof is purified.

In some embodiments, a pharmaceutically acceptable salt of the peptide is provided. In some instances, the pharmaceutically acceptable salt is a chloride salt.

Variant or Modified Peptides

In various embodiments, the peptide includes two Cys that form one disulfide bond, the peptide includes four Cys that form two disulfide bonds, or the peptide includes six Cys that form three disulfide bonds.

In some peptides one or both members of one or both pairs of Cys residues which normally form a disulfide bond can be replaced by homocysteine, penicillamine, 3-mercaptoproline (Kolodziej et al. 1996 *Int J Pept Protein Res* 48:274); β,β dimethylcysteine (Hunt et al. 1993 *Int J Pept Protein Res* 42:249) or diaminopropionic acid (Smith et al. 1978 *J Med Chem* 21:117) to form alternative internal cross-links at the positions of the normal disulfide bonds. In other embodiments, the disulfide bonds may be replaced by hydrocarbon crosslinking (Schafmeister et al. 2000 J Am Chem Soc 122: 5891, Patgiri et al. 2008 Acc Chem Res 41:1289, Henchey et al. 2008 Curr Opin Chem Biol 12:692).

Production of Peptides

In one embodiment, peptides or precursor peptides of the invention can be produced recombinantly in any known protein expression system, including, without limitation, bacteria (e.g., *E. coli* or *Bacillus subtilis*), insect cell systems (e.g., *Drosophila* Sf9 cell systems), yeast cell systems (e.g., *S. cerevisiae, S. saccharomyces*) or filamentous fungal expression systems, or animal cell expression systems (e.g., mammalian cell expression systems). Peptides or precursor peptides of the invention may also be chemically synthesized.

If the peptide or variant peptide is to be produced recombinantly, e.g., *E. coli*, the nucleic acid molecule encoding the peptide may also encode a leader sequence that permits the secretion of the mature peptide from the cell. Thus, the sequence encoding the peptide can include the pre sequence and the pro sequence of, for example, a naturally-occurring bacterial ST peptide. The secreted, mature peptide can be purified from the culture medium.

The sequence encoding a peptide described herein can be inserted into a vector capable of delivering and maintaining the nucleic acid molecule in a bacterial cell. The DNA molecule may be inserted into an autonomously replicating vector (suitable vectors include, for example, pGEM3Z and pcDNA3, and derivatives thereof). The vector nucleic acid may be a bacterial or bacteriophage DNA such as bacteriophage lambda or M13 and derivatives thereof. Construction of a vector containing a nucleic acid described herein can be followed by transformation of a host cell such as a bacterium. Suitable bacterial hosts include but are not limited to, *E. coli, B. subtilis, Pseudomonas* and *Salmonella*. The genetic construct also includes, in addition to the encoding nucleic acid molecule, elements that allow expression, such as a promoter and regulatory sequences. The expression vectors may contain transcriptional control sequences that control transcriptional initiation, such as promoter, enhancer, operator, and repressor sequences. A variety of transcriptional control sequences are well known to those in the art. The expression vector can also include a translation regulatory sequence (e.g., an untranslated 5' sequence, an untranslated 3' sequence, or an internal ribosome entry site). The vector can be capable of autonomous replication or it can integrate into host DNA to ensure stability during peptide production.

The protein coding sequence that includes a peptide described herein can also be fused to a nucleic acid encoding a peptide affinity tag, e.g., glutathione S-transferase (GST), maltose E binding protein, protein A, FLAG tag, hexa-histidine, myc tag or the influenza HA tag, in order to facilitate purification. The affinity tag or reporter fusion joins the reading frame of the peptide of interest to the reading frame of the gene encoding the affinity tag such that a translational fusion is generated. Expression of the fusion gene results in translation of a single peptide that includes both the peptide of interest and the affinity tag. In some instances where affinity tags are utilized, DNA sequence encoding a protease recognition site will be fused between the reading frames for the affinity tag and the peptide of interest.

Genetic constructs and methods suitable for production of immature and mature forms of the peptides and variants described herein in protein expression systems other than bacteria, and well known to those skilled in the art, can also be used to produce peptides in a biological system.

In other embodiments, peptides containing amino acids not normally incorporated by the translation machinery and described above (e.g.—β-carboxylated Asp, γ-carboxylated Glu, Asu, Aad and Apm) may be recombinantly produced by tRNA modification methods. Methods for modifying tRNA including, but not limited to, modifying the anti-codon, the amino acid attachment site, and/or the accepter stem to allow incorporation of unnatural and/or arbitrary amino acids are known in the art (Biochem. Biophys. Res. Comm. (2008) 372: 480-485; Chem. Biol. (2009) 16:323-36; Nat. Methods (2007) 4:239-44; Nat. Rev. Mol. Cell Biol. (2006) 7:775-82;

Methods (2005) 36:227-238; Methods (2005) 36:270-278; Annu. Rev. Biochem. (2004) 73:147-176; Nuc. Acids Res. (2004) 32:6200-6211; Proc. Natl. Acad. Sci. USA (2003) 100:6353-6357; Royal Soc. Chem. (2004) 33:422-430).

In some embodiments, peptides may be chemically produced. Peptides can be synthesized by a number of different methods including solution and solid phase synthesis using traditional BOC or FMOC protection. For example, the peptide can be synthesized on 2-Chlorotrityl or Wang resin using consecutive amino acid couplings. The following protecting groups can be used: Fluorenylmethyloxycarbonyl or tert-butyloxycarbonyl (alpha-amino groups, N-terminus); trityl or tert-butyl (thiol groups of Cys); tert-butyl (γ-carboxyl of glutamic acid and the hydroxyl group of threonine, if present); and trityl (β-amid function of the asparagine side chain and the phenolic group of tyrosine, if present). Coupling can be effected with DIC and HOBt in the presence of a tertiary amine, and the peptide can be deprotected and cleaved from the solid support in using cocktail K (trifluoroacetic acid 81%, phenol 5%, thioanisole 5%, 1,2-ethanedithiol 2.5%, water 3%, dimethylsulphide 2%, ammonium iodide 1.5% w/w). After removal of trifluoroacetic acid and other volatiles the peptide can be precipitated using an organic solvent. Disulfide bonds between Cys residues can be formed using dimethyl sulfoxide (Tam et al. (1991) J. Am. Chem. Soc. 113:6657-62) or using an air oxidation strategy. The resulting peptide can be purified by reverse-phase chromatography and lyophilized.

These peptides can be made, isolated or used either in form of the base or as pharmaceutically acceptable salts thereof. Examples of salts include, without limitation, acetate, chloride, sulfate and phosphate salts of the peptide.

Compositions of Peptides and GC-C Receptor Agonists

In another aspect, pharmaceutical compositions are provided wherein the peptides, alone or in combination, can be combined with any pharmaceutically acceptable carrier or medium.

In several embodiments, the pharmaceutical composition comprises a peptide or pharmaceutically acceptable salt thereof as described herein. The pharmaceutical composition may comprise two or more peptides or pharmaceutically acceptable salts thereof described herein.

In some embodiments, the pharmaceutical composition comprises two or more peptides selected from:
i. a peptide or a pharmaceutically acceptable salt thereof, wherein the peptide comprises the amino acid structure of:

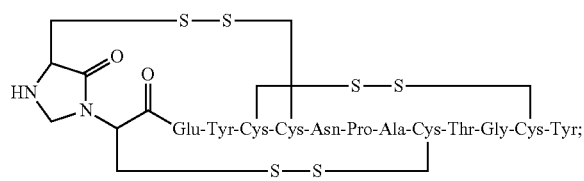

ii. a peptide or a pharmaceutically acceptable salt thereof, wherein the peptide comprises an amino acid structure of:

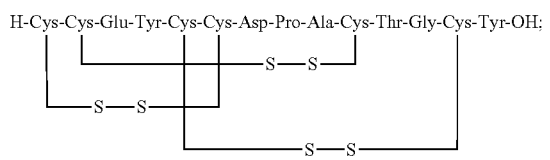

and iii. a peptide or a pharmaceutically acceptable salt thereof, wherein the peptide comprises the amino acid sequence Cys Cys Glu Tyr Cys Cys Asn Pro Ala Cys Thr Gly Cys Tyr (SEQ ID NO:1), wherein at least one carboxyl group of the peptide is an alkyl ester having the formula (—COOR) in which R is a $C_{1-6}$ alkyl.

In other embodiments, the pharmaceutical composition comprises linaclotide and a peptide or a pharmaceutically acceptable salt thereof, wherein the peptide comprises an amino acid structure of:

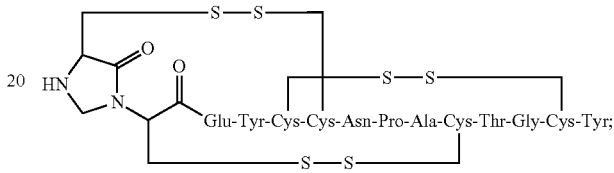

and the peptide or pharmaceutically acceptable salt thereof comprises less than 10%, 20%, 30%, 40%, 50%, 60%, 70%, 80%, or 90% by weight compared to the weight of linaclotide.

In further embodiments, the pharmaceutical composition comprises linaclotide and a peptide or a pharmaceutically acceptable salt thereof, wherein the peptide comprises an amino acid structure of:

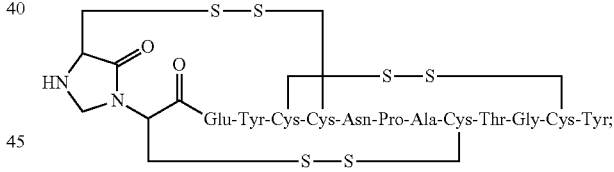

and the peptide or pharmaceutically acceptable salt thereof comprises less than 9%, 8%, 7%, 6%, 5%, 4%, 3%, 2%, or 1% by weight compared to the weight of linaclotide.

In some embodiments, the imidazolidinone derivative of linaclotide comprises less than about 15% by weight of the composition, less than about 10% by weight of the composition, less than about 7% by weight of the composition or less than about 5% by weight of the composition. In other exemplary embodiments, the imidazolidinone derivative of linaclotide comprises from about 0.01% to about 15% by weight of the composition, about 0.05% to about 10% by weight of the composition, about 0.05% to about 7% by weight of the composition or about 0.05% to about 5% by weight of the composition.

In other embodiments, the pharmaceutical composition comprises linaclotide and a peptide or a pharmaceutically acceptable salt thereof, wherein the peptide comprises an amino acid structure of:

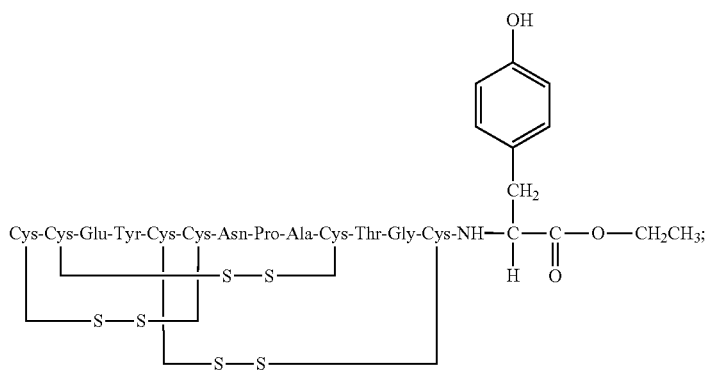

and the peptide or pharmaceutically acceptable salt thereof comprises less than 10%, 20%, 30%, 40%, 50%, 60%, 70%, 80%, or 90% by weight compared to the weight of linaclotide.

In further embodiments, the pharmaceutical composition comprises linaclotide and a peptide or a pharmaceutically acceptable salt thereof, wherein the peptide comprises an amino acid structure of:

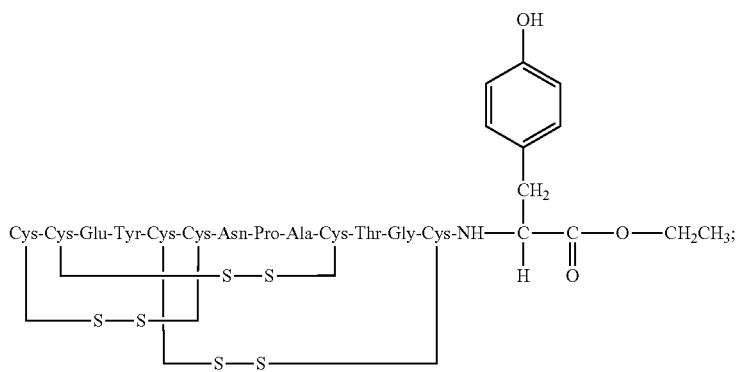

and the peptide or pharmaceutically acceptable salt thereof comprises less than 9%, 8%, 7%, 6%, 5%, 4%, 3%, 2%, or 1% by weight compared to the weight of linaclotide.

In some embodiments, the $Tyr_{14}$-ethyl ester peptide comprises less than about 15% by weight of the composition, less than about 10% by weight of the composition, less than about 7% by weight of the composition or less than about 5% by weight of the composition. In other exemplary embodiments, the $Tyr_{14}$-ethyl ester comprises from about 0.01% to about 15% by weight of the composition, about 0.05% to about 10% by weight of the composition, about 0.05% to about 7% by weight of the composition or about 0.05% to about 5% by weight of the composition.

In other embodiments, the pharmaceutical composition comprising linaclotide and a peptide or a pharmaceutically acceptable salt thereof, wherein the peptide comprises an amino acid structure of:

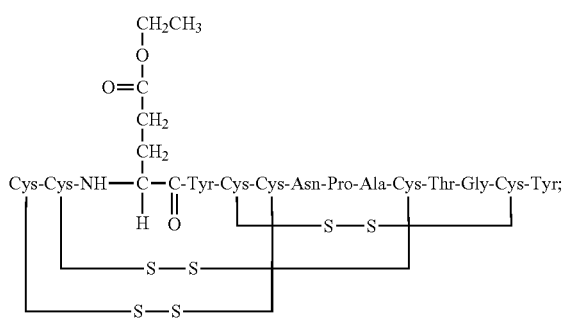

and the peptide or pharmaceutically acceptable salt thereof comprises less than 10%, 20%, 30%, 40%, 50%, 60%, 70%, 80%, or 90% by weight compared to the weight of linaclotide.

In further embodiments, the pharmaceutical composition comprises linaclotide and a peptide or a pharmaceutically acceptable salt thereof, wherein the peptide comprises an amino acid structure of:

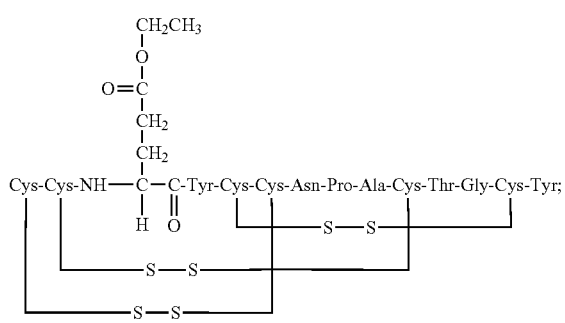

and the peptide or pharmaceutically acceptable salt thereof comprises less than 9%, 8%, 7%, 6%, 5%, 4%, 3%, 2%, or 1% by weight compared to the weight of linaclotide.

In some embodiments, the Glu$_3$-ethyl ester peptide comprises less than about 15% by weight of the composition, less than about 10% by weight of the composition, less than about 7% by weight of the composition or less than about 5% by weight of the composition. In other exemplary embodiments, the Glu$_3$-ethyl ester comprises from about 0.01% to about 15% by weight of the composition, about 0.05% to about 10% by weight of the composition, about 0.05% to about 7% by weight of the composition or about 0.05% to about 5% by weight of the composition.

In some embodiments, the pharmaceutical composition comprises a peptide or pharmaceutically acceptable salt, wherein the peptide consists of the amino acid structure of:

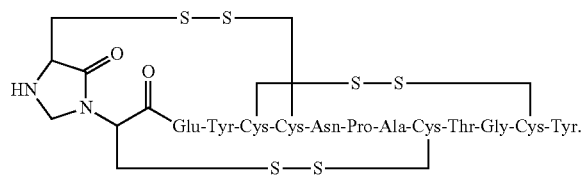

In other embodiments, the pharmaceutical composition consists essentially of a peptide or pharmaceutically acceptable salt thereof, wherein the peptide comprises the amino acid structure of:

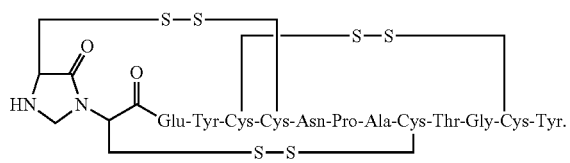

The term "consisting essentially of", and variants thereof, when used to refer to the composition, are used herein to mean that the composition includes a sole active peptide and other desired pharmaceutically inactive additives, excipients, and/or components (e.g., polymers, sterically hindered primary amines, cations, filling agents, binders, carriers, excipients, diluents, disintegrating additives, lubricants, solvents, dispersants, coating additives, absorption promoting additives, controlled release additives, anti-caking additives, anti-microbial additives, preservatives, sweetening additives, colorants, flavors, desiccants, plasticizers, dyes, or the like), and no other active pharmaceutical ingredient(s).

The peptides described herein can be combined with any pharmaceutically tolerable carrier or medium, e.g. solvents, dispersants, coatings, absorption promoting agents, controlled release agents, and one or more inert excipients (which include starches, polyols, granulating agents, microcrystalline cellulose (e.g. celphere, Celphere Beads®), diluents, lubricants, binders, disintegrating agents, and the like), etc. If desired, tablet dosages of the disclosed compositions may be coated by standard aqueous or nonaqueous techniques.

Examples of excipients for use as the pharmaceutically acceptable carriers and the pharmaceutically acceptable inert carriers and the aforementioned additional ingredients include, but are not limited to binders, fillers, disintegrants, lubricants, anti-microbial agents, and coating agents.

As used herein, the term "binder" refers to any pharmaceutically acceptable binder that may be used in the practice of the invention. Examples of pharmaceutically acceptable binders include, without limitation, a starch (e.g., corn starch, potato starch and pre-gelatinized starch (e.g., STARCH 1500® and STARCH 1500 LM®, sold by Colorcon, Ltd.) and other starches), maltodextrin, gelatin, natural and synthetic gums such as acacia, powdered tragacanth, guar gum, cellulose and its derivatives (e.g., methylcellulose, hydroxyethyl cellulose, hydroxyethyl methylcellulose, hydroxypropyl cellulose and hydroxypropyl methylcellulose (hypromellose), ethyl cellulose, cellulose acetate, carboxymethyl cellulose calcium, sodium carboxymethyl cellulose, carboxymethylcellulose, microcrystalline cellulose (e.g. AVICEL™, such as, AVICEL-PH-101™, -103™ and -105™, sold by FMC Corporation, Marcus Hook, Pa., USA)), polyvinyl alcohol, polyvinyl pyrrolidone (e.g., polyvinyl pyrrolidone K30), and mixtures thereof.

As used herein, the term "filler" refers to any pharmaceutically acceptable filler that may be used in the practice of the invention. Examples of pharmaceutically acceptable fillers include, without limitation, talc, calcium carbonate (e.g., granules or powder), dibasic calcium phosphate, tribasic calcium phosphate, calcium sulfate (e.g., granules or powder), microcrystalline cellulose (e.g., Avicel PH101 or Celphere CP-305), powdered cellulose, dextrates, kaolin, mannitol, silicic acid, sorbitol, starch (e.g., Starch 1500), pre-gelatinized starch, lactose, glucose, fructose, galactose, trehalose, sucrose, maltose, isomalt, raffinose, maltitol, melezitose, stachyose, lactitol, palatinite, xylitol, myoinositol, and mixtures thereof.

Examples of pharmaceutically acceptable fillers that may be particularly used for coating the peptides include, without limitation, talc, microcrystalline cellulose (e.g., Avicel PH101 or Celphere CP-305), powdered cellulose, dextrates, kaolin, mannitol, silicic acid, sorbitol, starch, pre-gelatinized starch, lactose, glucose, fructose, galactose, trehalose, sucrose, maltose, isomalt, dibasic calcium phosphate, raffinose, maltitol, melezitose, stachyose, lactitol, palatinite, xylitol, mannitol, myoinositol, and mixtures thereof.

As used herein, the term "additives" refers to any pharmaceutically acceptable additive. Pharmaceutically acceptable additives include, without limitation, disintegrants, dispersing additives, lubricants, glidants, antioxidants, coating additives, diluents, surfactants, flavoring additives, humectants, absorption promoting additives, controlled release additives, anti-caking additives, anti-microbial agents (e.g., preservatives), colorants, desiccants, plasticizers and dyes. As used herein, an "excipient" is any pharmaceutically acceptable additive, filler, binder or agent.

Compositions of the present invention may also optionally include other therapeutic ingredients, anti-caking agents, preservatives, sweetening agents, colorants, flavors, desiccants, plasticizers, dyes, glidants, anti-adherents, anti-static agents, surfactants (wetting agents), anti-oxidants, film-coating agents, and the like. Any such optional ingredient must be compatible with the compound described herein to insure the stability of the formulation. The composition may contain other additives as needed, including for example lactose, glucose, fructose, galactose, trehalose, sucrose, maltose, raffinose, maltitol, melezitose, stachyose, lactitol, palatinite, starch, xylitol, mannitol, myoinositol, and the like, and hydrates thereof, and amino acids, for example alanine, glycine and betaine, and peptides and proteins, for example albumen.

The compositions can include, for example, various additional solvents, dispersants, coatings, absorption promoting additives, controlled release additives, and one or more inert additives (which include, for example, starches, polyols, granulating additives, microcrystalline cellulose, diluents, lubricants, binders, disintegrating additives, and the like), etc. If desired, tablet dosages of the disclosed compositions may be coated by standard aqueous or non-aqueous techniques. Compositions can also include, for example, anti-caking additives, preservatives, sweetening additives, colorants, flavors, desiccants, plasticizers, dyes, and the like.

Suitable disintegrants include, for example, agar-agar, calcium carbonate, microcrystalline cellulose, croscarmellose sodium, crospovidone, povidone, polacrilin potassium, sodium starch glycolate, potato or tapioca starch, other starches, pre-gelatinized starch, clays, other algins, other celluloses, gums, and mixtures thereof.

Suitable lubricants include, for example, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil and soybean oil), zinc stearate, ethyl oleate, ethyl laurate, agar, syloid silica gel (AEROSIL 200, W.R. Grace Co., Baltimore, Md. USA), a coagulated aerosol of synthetic silica (Evonik Degussa Co., Plano, Tex. USA), a pyrogenic silicon dioxide (CAB-O-SIL, Cabot Co., Boston, Mass. USA), and mixtures thereof.

Suitable glidants include, for example, leucine, colloidal silicon dioxide, magnesium trisilicate, powdered cellulose, starch, talc, and tribasic calcium phosphate.

Suitable anti-caking additives include, for example, calcium silicate, magnesium silicate, silicon dioxide, colloidal silicon dioxide, talc, and mixtures thereof.

Suitable anti-microbial additives that may be used, e.g., as a preservative for the peptides compositions, include, for example, benzalkonium chloride, benzethonium chloride, benzoic acid, benzyl alcohol, butyl paraben, cetylpyridinium chloride, cresol, chlorobutanol, dehydroacetic acid, ethylparaben, methylparaben, phenol, phenylethyl alcohol, phenoxyethanol, phenylmercuric acetate, phenylmercuric nitrate, potassium sorbate, propylparaben, sodium benzoate, sodium dehydroacetate, sodium propionate, sorbic acid, thimersol, thymo, and mixtures thereof.

Suitable antioxidants include, for example, BHA (butylated hydroxyanisole), BHT (butylated hydroxytoluene), vitamin E, propyl gallate, ascorbic acid and salts or esters thereof, tocopherol and esters thereof, alpha-lipoic acid and beta-carotene.

Suitable coating additives include, for example, sodium carboxymethyl cellulose, cellulose acetate phthalate, ethylcellulose, gelatin, pharmaceutical glaze, hydroxypropyl cellulose, hydroxypropyl methylcellulose, hydroxypropyl methyl cellulose phthalate, methylcellulose, polyethylene glycol, polyvinyl acetate phthalate, shellac, sucrose, titanium dioxide, carnauba wax, microcrystalline wax, and mixtures thereof. Suitable protective coatings include Aquacoat (e.g. Aquacoat Ethylcellulose Aqueous Dispersion, 15% w/w, FMC Biopolymer, ECD-30), Eudragit (e.g. Eudragit E PO PE-EL, Roehm Pharma Polymers) and Opadry (e.g Opadry AMB dispersion, 20% w/w, Colorcon).

In certain embodiments, suitable additives for the peptides composition include one or more of sucrose, talc, magnesium stearate, crospovidone or BHA.

The compositions of the present invention can also include other excipients, agents, and categories thereof including but not limited to L-histidine, Pluronic®, Poloxamers (such as Lutrol® and Poloxamer 188), ascorbic acid, glutathione, permeability enhancers (e.g. lipids, sodium cholate, acylcarnitine, salicylates, mixed bile salts, fatty acid micelles, chelators, fatty acid, surfactants, medium chain glycerides), protease inhibitors (e.g. soybean trypsin inhibitor, organic acids), pH lowering agents and absorption enhancers effective to promote bioavailability (including but not limited to those described in U.S. Pat. No. 6,086,918 and U.S. Pat. No. 5,912,014), materials for chewable tablets (like dextrose, fructose, lactose monohydrate, lactose and aspartame, lactose and cellulose, maltodextrin, maltose, mannitol, microcrystalline cellulose and guar gum, sorbitol crystalline); parenterals (like mannitol and povidone); plasticizers (like dibutyl sebacate, plasticizers for coatings, polyvinylacetate phthalate); powder lubricants (like glyceryl behenate); soft gelatin capsules (like sorbitol special solution); spheres for coating (like sugar spheres); spheronization agents (like glyceryl behenate and microcrystalline cellulose); suspending/gelling agents (like carrageenan, gellan gum, mannitol, microcrystalline cellulose, povidone, sodium starch glycolate, xanthan gum); sweeteners (like aspartame, aspartame and lactose, dextrose, fructose, honey, maltodextrin, maltose, mannitol, molasses, sorbitol crystalline, sorbitol special solution, sucrose); wet granulation agents (like calcium carbonate, lactose anhydrous, lactose monohydrate, maltodextrin, mannitol, microcrystalline cellulose, povidone, starch), caramel, carboxymethylcellulose sodium, cherry cream flavor and cherry flavor, citric acid anhydrous, citric acid, confectioner's sugar, D&C Red No. 33, D&C Yellow #10 Aluminum Lake, disodium edetate, ethyl alcohol 15%, FD&C Yellow No. 6 aluminum lake, FD&C Blue #1 Aluminum Lake, FD&C Blue No. 1, FD&C blue no. 2 aluminum lake, FD&C Green No. 3, FD&C Red No. 40, FD&C Yellow No. 6 Aluminum Lake, FD&C Yellow No. 6, FD&C Yellow No. 10, glycerol palmitostearate, glyceryl monostearate, indigo carmine, lecithin, manitol, methyl and propyl parabens, mono ammonium glycyrrhizinate, natural and artificial orange flavor, pharmaceutical glaze, poloxamer 188, Polydextrose, polysorbate 20, polysorbate 80, polyvidone, pregelatinized corn starch, pregelatinized starch, red iron oxide, saccharin sodium, sodium carboxymethyl ether, sodium chloride, sodium citrate, sodium phosphate, strawberry flavor, synthetic black iron oxide, synthetic red iron oxide, titanium dioxide, and white wax.

In some embodiments, there is provided a pharmaceutical composition comprising a peptide described herein and one or more agents selected from $Mg^{2+}$, $Ca^{2+}$, $Zn^{2+}$, $Mn^{2+}$, $K^+$, $Na^+$ or $Al^{3+}$, a combination thereof, and/or a sterically hindered primary amine. In further embodiments, the agent is $Mg^{2+}$, $Ca^{2+}$ or $Zn^{2+}$ or a combination thereof. In some embodiments, the cation is provided, without limitation, as magnesium acetate, magnesium chloride, magnesium phosphate, magnesium sulfate, calcium acetate, calcium chloride, calcium phosphate, calcium sulfate, zinc acetate, zinc chloride, zinc phosphate, zinc sulfate, manganese acetate, manganese chloride, manganese phosphate, manganese sulfate, potassium acetate, potassium chloride, potassium phosphate, potassium sulfate, sodium acetate, sodium chloride, sodium phosphate, sodium sulfate, aluminum acetate, aluminum chloride, aluminum phosphate or aluminum sulfate. In further embodiments, the cation is provided as magnesium chloride, calcium chloride, calcium phosphate, calcium sulfate, zinc acetate, manganese chloride, potassium chloride, sodium chloride or aluminum chloride. In other embodiments, the cation is provided as calcium chloride, magnesium chloride or zinc acetate.

In another embodiment, the agent is a sterically hindered primary amine. In a further embodiment, the sterically hindered primary amine is an amino acid. In yet a further embodiment, the amino acid is a naturally-occurring amino acid. In a still further embodiment, the naturally-occurring amino acid is selected from the group consisting of: histidine, phenylalanine, alanine, glutamic acid, aspartic acid, glutamine, leucine, methionine, asparagine, tyrosine, threonine, isoleucine, tryptophan, glycine and valine; yet further, the naturally-occurring amino acid is leucine, isoleucine, alanine or methionine. In a still further embodiment, the naturally-occurring amino acid is leucine. In another embodiment, the sterically hindered primary amine is a non-naturally occurring amino acid (e.g., 1-aminocyclohexane carboxylic acid). In a further embodiment, the sterically hindered primary amine is cyclohexylamine, 2-methylbutylamine or chitosan. In another embodiment, one or more sterically hindered primary amines may be used in a composition.

In some cases, the sterically hindered primary amine has the formula:

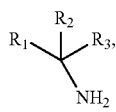

wherein $R_1$, $R_2$ and $R_3$ are independently selected from: H, C(O)OH, C1-C6 alkyl, C1-C6 alkylether, C1-C6 alkylthioether, C1-C6 alkyl carboxylic acid, C1-C6 alkyl carboxylamide and alkylaryl, wherein any group can be singly or multiply substituted with: halogen or amino, and provided that no more than two of $R_1$, $R_2$ and $R_3$ are H. In another embodiment, no more than one of $R_1$, $R_2$ and $R_3$ is H.

In other embodiments, there is provided a pharmaceutical composition comprising a pharmaceutically acceptable carrier, peptide, a cation selected from $Mg^{2+}$, $Ca^{2+}$, $Zn^{2+}$, $Mn^{2+}$, $K^+$, $Na^+$ or $Al^{3+}$, or a mixture thereof, and a sterically hindered primary amine. In one embodiment, the cation is $Mg^{2+}$, $Ca^{2+}$ or $Zn^{2+}$ or a mixture thereof. In a further embodiment, the pharmaceutical composition further comprises a pharmaceutically acceptable binder and/or a pharmaceutically acceptable glidant, lubricant or additive that acts as both a glidant and lubricant and/or an antioxidant. In some embodiments, the pharmaceutical composition is applied to a carrier. In some embodiments, the carrier is a filler.

In some cases the molar ratio of cation:sterically hindered primary amine: peptide in the aqueous solution applied to the carrier is 5-100:5-50:1. In some cases, the molar ratio of cation:sterically hindered primary amine may be equal to or greater than 2:1 (e.g., between 5:1 and 2:1). Thus, in some cases the molar ratio of cation:sterically hindered primary amine: peptide applied to the carrier is 100:50:1, 100:30:1, 80:40:1, 80:30:1, 80:20:1, 60:30:1, 60:20:1, 50:30:1, 50:20:1, 40:20:1, 20:20:1, 10:10:1, 10:5:1 or 5:10:1. When binder, e.g., methylcellulose, is present in the GC-C agonist peptide solution applied to the carrier it can be present at 0.5%-2.5% by weight (e.g., 0.7%-1.7% or 0.7%-1% or 1.5% or 0.7%).

In a further embodiment, the pharmaceutical composition further comprises a pharmaceutically acceptable binder or additive, and/or a pharmaceutically acceptable glidant, lubricant or additive that acts as both a glidant and lubricant and/or an antioxidant.

Suitable pharmaceutical compositions in accordance with the invention will generally include an amount of the active compound(s) with an acceptable pharmaceutical diluent or excipient, such as a sterile aqueous solution, to give a range of final concentrations, depending on the intended use. The techniques of preparation are generally well known in the art, as exemplified by Remington's Pharmaceutical Sciences (18th Edition, Mack Publishing Company, 1995).

The compositions described herein may be administered systemically or locally, e.g.: orally (e.g. using capsules, powders, solutions, suspensions, tablets, sublingual tablets and the like), by inhalation (e.g. with an aerosol, gas, inhaler, nebulizer or the like), to the ear (e.g. using ear drops), topically (e.g. using creams, gels, liniments, lotions, ointments, pastes, transdermal patches, etc), ophthalmically (e.g. with eye drops, ophthalmic gels, ophthalmic ointments), rectally (e.g. using enemas or suppositories), nasally, buccally, vaginally (e.g. using douches, intrauterine devices, vaginal suppositories, vaginal rings or tablets, etc), via an implanted reservoir or the like, or parenterally depending on the severity and type of the disease being treated. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

For treatment of gastrointestinal disorders, the peptides described herein are preferably administered orally, e.g., as a tablet, capsule, sachet containing a predetermined amount of the active ingredient pellet, gel, paste, syrup, bolus, electuary, slurry, powder, lyophilized powder, granules, as a solution or a suspension in an aqueous liquid or a non-aqueous liquid; as an oil-in-water liquid emulsion or a water-in-oil liquid emulsion, via a liposomal formulation (see, e.g., EP 736299) or in some other form. Orally administered compositions can include binders, lubricants, inert diluents, lubricating, surface active or dispersing agents, flavoring agents, and humectants. Orally administered formulations such as tablets may optionally be coated or scored and may be formulated so as to provide sustained, delayed or controlled release of the active ingredient therein.

The peptides can be co-administered with other agents used to treat gastrointestinal disorders including but not limited to the agents described herein.

In another aspect, suitable pharmaceutical compositions may comprise one or more other therapeutic agents. Such therapeutic agents include, without limitation, analgesic agents; anti-secretory agents, including proton pump inhibitors, acid pump antagonists, H2 receptor antagonists; PDE5 inhibitors; GABA-B antagonists; bile acid sequestrants; prokinetic and promotility agents; antidepressants; antibiotics; antiemetics; and mucosal-protecting agents.

Methods of Treatment

In various embodiments, the peptides and compositions described herein are useful for the treatment of patient gastrointestinal disorder.

In some embodiments, the gastrointestinal disorder is selected from the group consisting of irritable bowel syndrome (IBS), constipation, a functional gastrointestinal disorder, gastroesophageal reflux disease, functional heartburn, dyspepsia, visceral pain, gastroparesis, chronic intestinal pseudo-obstruction, colonic pseudo-obstruction, Crohn's disease, ulcerative colitis, and inflammatory bowel disease.

In a further embodiment, the gastrointestinal disorder is constipation. The constipation can be chronic constipation, idiopathic constipation, due to post-operative ileus, or caused by opiate use. Clinically accepted criteria that define constipation include the frequency of bowel movements, the consistency of feces and the ease of bowel movement. One common definition of constipation is less than three bowel movements per week. Other definitions include abnormally hard stools or defecation that requires excessive straining (Schiller 2001, Aliment Pharmacol Ther 15:749-763). Constipation may be idiopathic (functional constipation or slow transit constipation) or secondary to other causes including neurologic, metabolic or endocrine disorders. These disorders include diabetes mellitus, hypothyroidism, hyperthyroidism, hypocalcaemia, Multiple Sclerosis, Parkinson's disease, spinal cord lesions, Neurofibromatosis, autonomic neuropathy, Chagas disease, Hirschsprung's disease and Cystic fibrosis. Constipation may also be the result of surgery (postoperative ileus) or due to the use of drugs such as analgesics (like opioids), antihypertensives, anticonvulsants, antidepressants, antispasmodics and antipsychotics.

In other embodiments, the gastrointestinal disorder is irritable bowel syndrome (IBS). The irritable bowel syndrome can be constipation-predominant irritable bowel syndrome (c-IBS), diarrhea-predominant irritable bowel syndrome (d-IBS) or alternating between the two irritable bowel syndromes (a-IBS).

In other embodiments, the gastrointestinal disorder is dyspepsia.

In other embodiments, the gastrointestinal disorder is gastroparesis. The gastroparesis can be selected from idiopathic, diabetic or post-surgical gastroparesis.

In still other embodiments, the gastrointestinal disorder is chronic intestinal pseudo obstruction.

In other embodiments, the gastrointestinal disorder is Crohn's disease.

In some embodiments, the gastrointestinal disorder is ulcerative colitis.

In some embodiments, the gastrointestinal disorder is inflammatory bowel disease.

In another embodiment, the gastrointestinal disorder is visceral pain. In a further embodiment, the present invention features a method for decreasing gastrointestinal pain or visceral pain in a patient, the method comprising, administering to the patient a pharmaceutical composition comprising of peptide described herein. The peptide agonists described herein can be used alone or in combination therapy for the treatment, prevention or reduction of visceral pain associated with a gastrointestinal disorder or pain associated with another disorder.

In another embodiment, the invention features a method for treating inflammation, including inflammation of the gastrointestinal tract, e.g., inflammation associated with a gastrointestinal disorder or infection or some other disorder, the method comprising administering to a patient a pharmaceutical composition comprising a purified peptide described herein.

In another embodiment, the invention features a method for treating a gastrointestinal disorder comprising administering an agonist of the intestinal guanylate cyclase (GC-C) receptor either orally, by rectal suppository, or parenterally.

In still another embodiment, the invention features a method for treating a gastrointestinal disorder comprising administering an agonist of the intestinal guanylate cyclase (GC-C) receptor.

In another aspect, the invention features a method of increasing the level of cyclic guanosine 3'-monophosphate (cGMP) in a biological sample, tissue (e.g, the intestinal mucosa), or cell (e.g., a cell bearing GC-A receptor), or whole organism by contacting the sample, tissue, or organism to a peptides described herein.

The peptide GC-C receptor agonists described herein can be administered in combination with other agents. For example, the peptides can be administered with an analgesic peptide or compound. The analgesic peptide or compound can be covalently attached to a peptide described herein or it can be a separate agent that is administered together with or sequentially with a peptide described herein in a combination therapy. The peptides described herein may also be administered in combination with other agents used to treat GI disorders including antidepressants, promotility or prokinetic agents, antiemetics, antibiotics, proton pump inhibitors, acid blockers (e.g., histamine 112 receptor antagonists), acid pump antagonists, PDE5 inhibitors, GABA-B agonists, bile acid sequestrants, and mucosal protecting agents.

In some embodiments, useful analgesic agents that may be used with the peptides described herein include Ca channel blockers (e.g., ziconotide), 5HT receptor antagonists (e.g., 5HT3, 5HT4 and 5HT1 receptor antagonists), 5HT4 agonists (e.g., tegaserod [Zelnorm®], mosapride, zacopride, cisapride, renzapride, prucalopride [Resolor®], benzimidazolone derivatives such as BIMU 1 and BIMU 8, and lirexapride), 5HT1 agonists (e.g., sumatriptan and buspirone), opioid receptor agonists (e.g., loperamide, fedotozine, enkephalin pentapeptide, morphine, diphenyloxylate, frakefamide, trimebutine and fentanyl), CCK receptor agonists (e.g., loxiglumide and dexloxiglumide), NK1 receptor antagonists (e.g., aprepitant, vofopitant, ezlopitant, R-673 (Hoffmann-La Roche Ltd), SR-48968 and SR-14033, (Sanofi Synthelabo), CP-122,721 (Pfizer, Inc.), GW679769 (Glaxo Smith Kline) and TAK-637 (Takeda/Abbot)), NK2 receptor antagonists (e.g., nepadutant, saredutant, GW597599 (Glaxo Smith Kline), SR-144190 (Sanofi-Synthelabo) and UK-290795 (Pfizer Inc)), NK3 receptor antagonists (e.g., osanetant (SR-142801; Sanofi-Synthelabo), SR-241586 and talnetant), norepinephrine-serotonin reuptake inhibitors (NSRI) (e.g., milnacipran), mixed and selective dopamine receptor antagonists (e.g. —metoclopramide, itopride, domperidone), vanilloid and cannabanoid receptor agonists, sialorphin and sialorphin-related peptides. Analgesics agents in the various classes are described in the literature.

In some embodiments, one or more other therapeutic agents may be used in combination with the peptides described herein. Such agents include antidepressants, promotility or prokinetic agents, antiemetics, antibiotics, proton pump inhibitors, acid blockers (e.g., histamine H2 receptor antagonists), acid pump antagonists, PDE5 inhibitors, GABA-B agonists, bile acid sequestrants, and mucosal protecting agents.

Examples of antidepressants include, without limitation, tricyclic antidepressants such as amitriptyline (Elavil®), desipramine (Norpramin®), imipramine (Tofranil®), amoxapine (Asendin®), nortriptyline; the selective serotonin reuptake inhibitors (SSRI's) such as paroxetine (Paxil®), fluoxetine (Prozac®), sertraline (Zoloft®), and citralopram (Celexa®); and others such as doxepin (Sinequan®) and trazodone (Desyrel®).

Examples of promotility and prokinetic agents include, without limitation, itopride, octreotide, bethanechol, metoclopramide (Reglan®), domperidone (Motilium®), erythromycin (and derivatives thereof) and cisapride (Propulsid®). An example of antiemetics includes, without limitation, prochlorperazine.

Examples of antibiotics that may be used include those that may be used to treat *Heliobacter pylori* infections, such as amoxicillin, tetracycline, metronidazole, or clarithromycin. Other antibiotics such as erythromycin and derivatives thereof may also be used in combination with the peptides described herein.

Examples of proton pump inhibitors include, without limitation, omeprazole (Prilosec®), esomeprazole (Nexium®), lansoprazole (Prevacid®), pantoprazole (Protonix®) and rabeprazole (Aciphex®). Examples of H2 receptor blockers include, without limitation, including cimetidine, ranitidine, famotidine and nizatidine. Examples of acid pump antagonists include, without limitation, revaprazan, CS-526 (J. Pharmacol. Exp. Ther. (2007) 323:308-317), PF-03716556 (J. Pharmacol. Exp. Ther. (2009) 328(2):671-9), and YH1885 (Drug Metab. Dispos. (2001) 29(1):54-9).

Examples of PDE5 inhibitors include, without limitation, avanafil, lodenafil, mirodenafil, sildenafil citrate, tadalafil, vardenafil and udenafil. GABA-B agonists include, without limitation, baclofen and XP19986 (CAS Registry No. 847353-30-4). Examples of bile acid sequestrants include, without limitation, GT102-279, cholestyramine, colesevelam, colesevelam hydrochloride, ursodeoxycholic acid, colestipol, colestilan, sevelamer, polydiallylamine cross-linked with epichlorohydrin, dialkylaminoalkyl derivatives of a cross-linked dextran, and N-(cycloalkyl)alkylamines. Examples of mucosal protecting agents include, without limitation, sucralfate (Carafate), teprenone, polaprezinc, cetraxate and bismuth subsalicyclate.

Combination therapy can be achieved by administering two or more agents, e.g., a peptide described herein and another therapeutic peptide or compound, each of which is formulated and administered separately, or by administering two or more agents in a single formulation. Other combinations are also encompassed by combination therapy. For example, two agents can be formulated together and administered in conjunction with a separate formulation containing a third agent. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within 1, 2, 3, 6, 9, 12, 15, 18, or 24 hours of each other or within 1, 2, 3, 4, 5, 6, 7, 8, 9, 10, 12, 14 days of each other or within 2, 3, 4, 5, 6, 7, 8, 9, or 10 weeks of each other. In some cases even longer intervals are possible. While in many cases it is desirable that the two or more agents used in a combination therapy be present in within the patient's body at the same time, this need not be so.

Dosage

The dose range for adult humans may be generally from 5 μg to 100 mg/day orally of the peptides described herein. Tablets, capsules, or other forms of presentation provided in discrete units may conveniently contain an amount of compound described herein which is effective at such dosage or as a multiple of the same, for instance, units containing 25 μg to 2 mg or around 100 μg to 1 mg. The precise amount of compound prescribed to a patient will be the responsibility of the attendant physician. However, the dose employed will depend on a number of factors, including the age and sex of the patient, the precise disorder being treated, and its severity.

In various embodiments, the dosage unit is administered with food at anytime of the day, without food at anytime of the day, with food after an overnight fast (e.g. with breakfast), at bedtime after a low fat snack. In one particular embodiment, the dosage unit is administered prior to or subsequent to food consumption (e.g., a meal). In a further embodiment, the dosage unit is administered approximately 15 minutes to 1 hour prior to food consumption. In various embodiments, the dosage unit is administered once a day, twice a day, three times a day, four times a day, five times a day or six times a day. In certain embodiments the dosage unit and daily dose are equivalent.

The precise amount of each of the two or more active ingredients in a dosage unit will depend on the desired dosage of each component. Thus, it can be useful to create a dosage unit that will, when administered according to a particular dosage schedule (e.g., a dosage schedule specifying a certain number of units and a particular timing for administration), deliver the same dosage of each component as would be administered if the patient was being treated with only a single component. In other circumstances, it might be desirable to create a dosage unit that will deliver a dosage of one or more components that is less than that which would be administered if the patient was being treated only with a single component. Finally, it might be desirable to create a dosage unit that will deliver a dosage of one or more components that is greater than that which would be administered if the patient was being treated only with a single component.

The pharmaceutical composition can include additional ingredients including but not limited to the excipients described herein. In certain embodiments, one or more therapeutic agents of the dosage unit may exist in an extended or control release formulation and additional therapeutic agents may not exist in extended release formulation. For example, a peptide or agonist described herein may exist in a controlled release formulation or extended release formulation in the same dosage unit with another agent that may or may not be in either a controlled release or extended release formulation. Thus, in certain embodiments, it may be desirable to provide for the immediate release of one or more of the agents described herein, and the controlled release of one or more other agents.

The present invention has been described with reference to certain exemplary embodiments thereof. However, it will be readily apparent to those skilled in the art that it is possible to embody the invention in specific forms other than those of the exemplary embodiments described above. This may be done without departing from the spirit of the invention. The exemplary embodiments are merely illustrative and should not be considered restrictive in any way. The scope of the invention is defined by the appended claims and their equivalents, rather than by the preceding description.

EXAMPLES

The GC-C agonist peptides or pharmaceutically acceptable salts thereof as described herein were prepared by solid phase chemical synthesis and natural folding (air oxidation) by American Peptide Company (Sunnyvale, Calif.). In some cases, the peptides were modified after synthesis as described herein.

The $Cys_1$-IMD peptide was synthesized by mixing 4.6 g (3.0 mmol) of linaclotide in 200 ml of EtOH. Formaldehyde at 37% (1.12 ml/5 eq) was added to this mixture. The reaction mixture was incubated in a water bath (45° C.) for overnight. The following day the solvent was removed by rota-evaporation. The peptide was further purified through reverse-phase chromatography.

The Glu$_3$-ethyl ester peptide was synthesized on a 20 mmol Fmoc-Tyr(tBu)-Wang resin. Protecting groups used for amino acids are: t-Butyl group for Tyr and Thr, Trt group for Asn and Cys. The peptide chain was assembled on the resin by repetitive removal of the Fmoc protecting group and coupling of protected amino acid. DIC and HOBt were used as coupling reagents and NMM was used as the base for this reaction. 20% piperidine in DMF was used as de-Fmoc-reagent. After removal of last Fmoc protecting group, resin was treated with cocktail K for 3 hours to cleave the peptide from resin and removal of the side chain protecting groups. The eluted peptide was precipitated in cold ether and dried. The dried peptide was dissolved in a mixture of TFA/TIS/water (95:3:2v/v) in a ratio of 1 to 10 (g/v). This mixture was stirred at room temperature for 1 hour. The isolated peptide was also precipitated in cold ether, collected by filtration and dried under high vacuum.

The Tyr$_{14}$-ethyl ester peptide was synthesized by a fragment condensation method. Fragment A (Boc-Cys(Trt)-Cys(Trt)-Glu(OtBu)-Tyr(tBu)-Cys(Trt)-Cys(Trt)-Asn(Trt)-Pro-Ala-Cys(Trt)-Thr(tBu)-Gly-OH) was prepared on 15 mmol CTC resin using Fmoc chemistry. This peptide chain was also assembled on the resin by repetitive removal of the Fmoc protecting group and coupling of protected amino acid. DIC and HOBt were used as coupling reagents and NMM was used as the base. 20% piperidine in DMF was used as de-Fmoc-reagent. After removal of last Fmoc protecting group, Boc was coupled to protect the N-terminal amino group. The peptide resin was washed, dried, and treated with 1% TFA/DCM to cleave peptide from resin. Fragment B (Cys(Trt)-Tyr-OEt) was prepared from coupling of Fmoc-Cys(Trt)-OH and Tyr-OEt. HCl. The Fmoc group was removed by treating this di-peptide with 20% piperidine in DMF.

The Tyr$_{14}$-ethyl ester peptide was finally synthesized by coupling the two fragments in DMF. HBTU/HOBt/NMM was used as the coupling reagent for this reaction. The protecting groups were removed by treating the peptide with cocktail K for 2 hours. This peptide was precipitated in cold ether and dried. The dried peptide was dissolved in a mixture of TFA/TIS/water (95:3:2v/v) in a ratio of 1 to 10 (g/v). This mixture was stirred at room temperature for 1 hour. The isolated peptide was again precipitated in cold ether, collected by filtration and dried under high vacuum.

Example 1 cGMP Accumulation in T84 Cells for Analysis of GC-C Activity

For the cGMP assay, 4.5×10$^5$ cells/mL of T84 cells were grown overnight in 24 well tissue culture plates. On next day, the T84 cells were washed twice with 1 mL of DMEM (pH 7). After the second wash, the cells were incubated with 450 μL of 1 mM isobutylmethylxanthine (IBMX) in pH 7 buffer for 10 minutes at 37° C. to inhibit any phosphodiesterase activity. The peptides were then diluted in DMEM buffer (pH 7) to a 10× concentration. The peptide solution of 50 μL was diluted to a final volume of 500 μL with the T84 cells, bringing each peptide concentration to lx. The peptides were tested in duplicate at 100 nM.

There was no peptide control used to determine endogenous levels of cGMP. Peptides were incubated for 30 minutes at 37° C. After 30 minutes, the supernatants were removed and the cells were lysed with 0.1 M HCl. The cells were lysed for 30 minutes on ice. After 30 minutes, lysates were pipetted off and placed into a 96 well HPLC plate and spun at 10,000×G for 10 minutes to remove any cell debris. Supernatants from the previous spin were removed and placed into a fresh 96 well HPLC plate.

cGMP concentrations were determined from each sample using the LC/MS conditions (Table 1 below) and calculated standard curve. EC$_{50}$ values were calculated from concentration-response curves generated with GraphPad Prism Software.

TABLE 1

| LC/MS conditions | |
|---|---|
| MS: | Thermo Quantum |
| Ion Mode: | ESI$^+$ |
| Scan Type: | MRM |

| Compound: | Transition | Dwell Time (msec) | Collision Energy (V) | Tube Lens | Retention Time (min) |
|---|---|---|---|---|---|
| cGMP | 346 > 152 | 100 | 28 | 139 | 1.0 |

| | |
|---|---|
| HPLC: | Agilent Technologies 1200 Series with CTC Analytics HTS PAL |
| Column: | Thermo Hypersil Gold 2.1 × 50 mm 5 micron particle size |
| Flow Rate: | 400 uL/min |
| Column Temperature: | RT |
| Autosampler Temperature: | 6° C. |
| Injection Volume: | 20 uL |
| Mobile Phases: | A = 98:2 Water:Acetonitrile + 0.1% Formic Acid |
| | B = 2:98 Water:Acetonitrile + 0.1% Formic Acid |

| | Time (min) | % A | % B |
|---|---|---|---|
| Gradient: | 0 | 100 | 0 |
| | 0.3 | 30 | 70 |
| | 2.00 | 30 | 70 |
| | 2.01 | 100 | 0 |
| | 4 | 100 | 0 |

Example 2

Relative Binding Affinity of Exemplary Peptides to the GC-C Receptor of T84 Cells The relative binding affinities of linaclotide and Cys$_1$-IMD to the guanylate cyclase-C receptor (GC-C) were determined using a competitive-binding assay in which the peptides competed with a known GC-C agonist, porcine-derived heat-stable enterotoxin (pSTa), for binding sites on cell-surface GC-C receptors on human colonic epithelial (T84) cells. The pSTa was radiolabeled with $^{125}$I to enable measurement of its receptor binding. The competitive-binding assay was performed by adding various concentrations of each peptide (0.1 to 3,000 nM) to 0.20 mL reaction mixtures containing Dulbecco's modified Eagle's medium (DMEM), 0.5% bovine serum albumin (BSA), 2.0×10$^5$ T84 cells, and 170 pM [$^{125}$I]-pSTa (200,000 cpm). The data were used to construct competitive radioligand-binding curves and determine the relative binding affinities of linaclotide and Cys$_1$-IMD, as measured by their IC$_{50}$ and K$_i$ values.

Figure 3:
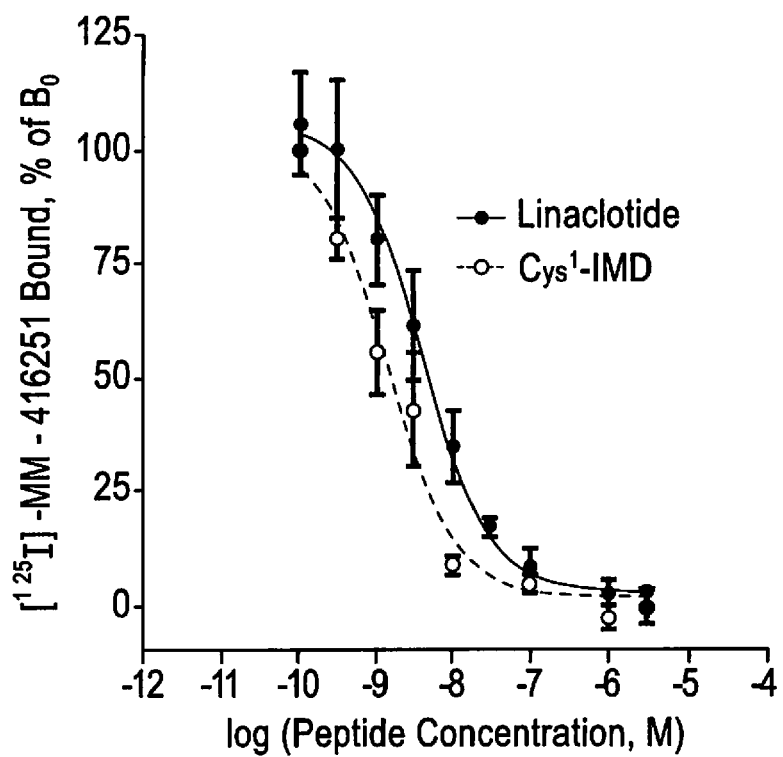
FIG. 3 shows specific binding of linaclotide and $Cys_1$-IMD to cell-surface GC-C receptors on T84 cells in a competitive radioligand binding assay.

Both linaclotide and Cys$_1$-IMD competitively inhibited the specific binding of [$^{125}$I]-pSTa to cell-surface GC-C receptors on T84 cells. Their relative binding affinities, as measured by their inhibition constants (K$_i$), were as follows: Linaclotide K$_i$=3.9±1.6 nM and Cys$_1$-IMD K$_i$=1.4±0.5 nM (FIG. 3).

Example 3 cGMP Response in T84 Cells Induced by Exemplary Peptides

Linaclotide and $Cys_1$-IMD were tested for guanylate cyclase-C (GC-C) agonist activity in T84 cells as follows. In each well of a 96-well plate, approximately 200,000 T84 cells/well was first incubated with 1 mM 3-isobutyl-1-methylxanthine (IBMX) in 0.18 mL of Dulbecco's modified Eagle's medium (DMEM) for 10 minutes at 37° C. Each peptide was diluted to final concentrations ranging from 0.1 to 10,000 nM, and 0.02 mL of each dilution was added in duplicate to a 96-well plate containing the T84 cells, for a final volume of 0.20 mL per well. The peptide reactions were incubated for 30 min at 37° C. Following the incubation, the supernatants were removed and discarded and the cells were lysed with cold 0.1 M hydrochloric acid (HCl) for 30 min on ice. The cell debris was removed by centrifugation and the concentration of guanosine 3',5'-cyclic monophosphate (cyclic GMP) in each lysate was determined using liquid chromatography with tandem mass spectrometry. The data were used to construct dose-response curves and calculate half-maximal effective concentration ($EC_{50}$) values for each test article.

Figure 4:
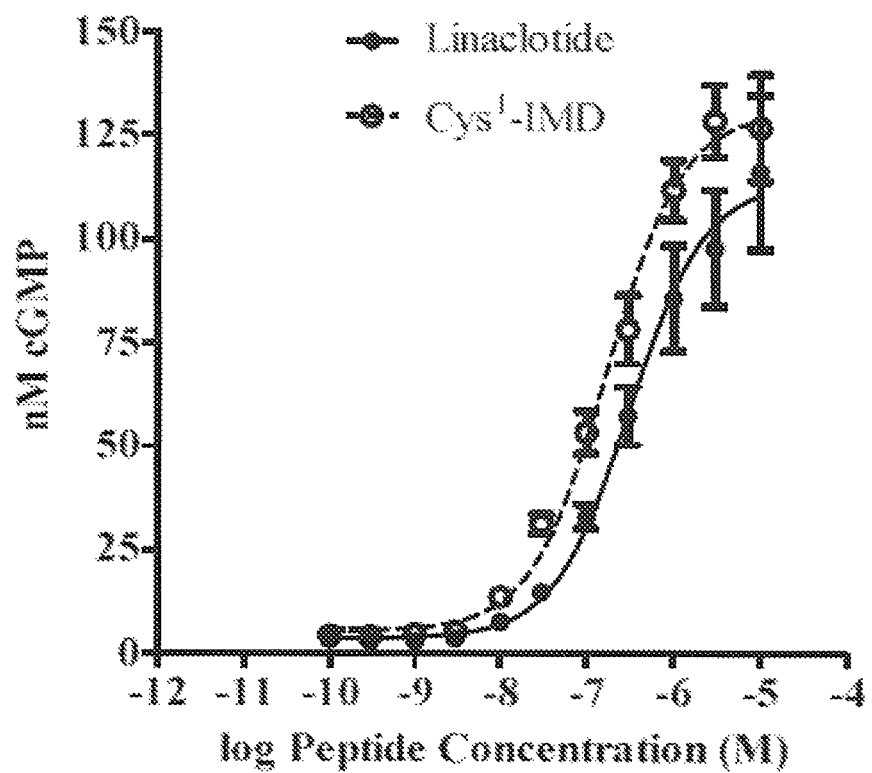
FIG. 4 shows the dose response of exemplary peptides of the present invention in a T84 cell c-GMP assay.

Linaclotide and $Cys_1$-IMD showed GC-C agonist activity in T84 cells, as measured by the increase in intracellular cGMP (FIG. 4). The $EC_{50}$ values for linaclotide and $Cys_1$-IMD were 315±105 nM and 172±32 nM, respectively.

Example 4

Measurement of Content and Purity of Exemplary Peptides

Content and purity of the peptides of the present invention may be determined by reverse phase gradient liquid chromatography using an Agilent Series 1100 LC System with Chemstation Rev A.09.03 software or equivalent. A YMC Pro™ C18 column (dimensions: 3.0×150 mm, 3.5 um, 120 Å; Waters Corp., Milford, Mass.) or equivalent is used and is maintained at 40° C. Mobile phase A (MPA) consists of water with 0.1% trifluoroacetic acid while mobile phase B (MPB) consists of 95% acetonitrile:5% water with 0.1% trifluoroacetic acid. Elution of the peptides is accomplished with a gradient from 0% to 47% MPB in 28 minutes followed by a ramp to 100% MPB in 4 minutes with a 5 minute hold at 100% MPB to wash the column. Re-equilibration of the column is performed by returning to 0% MPB in 1 minute followed by a 10 minute hold at 100% MPA. The flow rate is 0.6 mL/min and detection is accomplished by UV at 220 nm.

Samples for analysis are prepared by addition of the contents of capsules of exemplary peptides to 0.1 N HCl to obtain a target concentration of 20 μg peptide/mL. 100 μL of this solution is injected onto the column.

$Cys_1$-IMD Peptide

Figure 2:
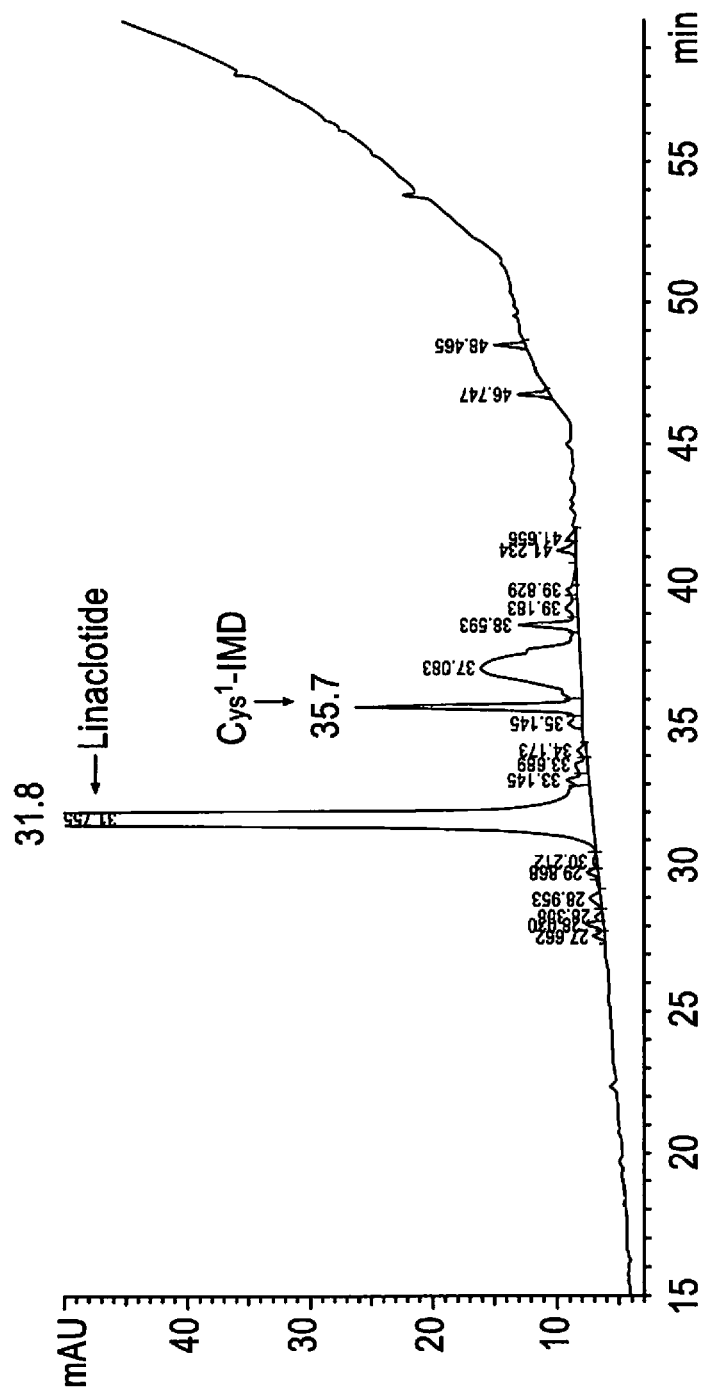
FIG. 2 demonstrates an example of an analysis of exemplary peptides by RP-HPLC, wherein "$Cys_1$-IMD" refers to the linaclotide imidazolidinone derivative modified on its N-terminal amine group.

The $Cys_1$-IMD peptide was purified using a 2-inch Waters C18 column with 0.1% TFA buffer with a linear gradient of 15-45% in 60 minutes of buffer B at flow rate of 100 mL/min. The pooled fractions with purity around 95% were loaded onto C18 column. After equilibrating the column with TEAP buffer and AA buffer, the peptide was purified and eluted out with HAC buffer with a linear gradient of 15-75% of buffer B in 60 minutes. Pooled fractions with purified peptide were lyophilized to dryness. An example of an analysis of linaclotide and $Cys_1$-IMD product by RP-HPLC is shown in FIG. 2.

$Glu_3$-Ethyl Ester Peptide

The $Glu_3$-ethyl ester peptide (6.0 g) was dissolved in 12 L of 0.05M ammonium bicarbonate in water, and the oxidation process was monitored by Ellman's test, MS and analytical HPLC. The oxidation process took approximately 48 hours for completion.

The above solution was filtered and loaded onto a 2-inch C18 column, and purified by using 0.05M ammonium acetate buffer with a linear gradient of 10-40% of buffer B in 60 minutes at flow rate of 100 mL/min.

The pooled fractions with purity of >95% were lyophilized to dryness. After the peptides were dried, the peptide was re-dissolved in acetonitrile-water and acidified to pH around 4-5 by addition of acetic acid and re-lyophilized to dryness.

$Tyr_1$-Ethyl Ester Peptide

The $Tyr_{14}$-ethyl ester peptide was purified by dissolving 2.5 g of the isolated peptide in 5 L of 0.05M ammonium bicarbonate in water, and the oxidation process was monitored by Ellman's test, MS and analytical HPLC. This oxidation process took approximately 16 hours for completion.

The above solution was filtered and loaded onto a 2-inch Polymer column, and purified by using 0.05M ammonium bicarbonate buffer with a linear gradient of 15-45% of buffer B in 60 minutes at flow rate of 100 mL/min. The pooled fractions with the peptide were lyophilized to dryness. After the peptide was dried, the peptide was re-dissolved in acetonitrile-water and acidified to pH 4-5 by addition of acetic acid and re-lyophilized to dryness.

The contents of the purified peptides were measured by determining the peptide concentration in the prepared sample against a similarly prepared external peptide standard.

Other Embodiments

All publications and patents referred to in this disclosure are incorporated herein by reference to the same extent as if each individual publication or patent application were specifically and individually indicated to be incorporated by reference. Should the meaning of the terms in any of the patents or publications incorporated by reference conflict with the meaning of the terms used in this disclosure, the meaning of the terms in this disclosure are intended to be controlling. Furthermore, the foregoing discussion discloses and describes merely exemplary embodiments of the present invention. One skilled in the art will readily recognize from such discussion and from the accompanying drawings and claims, that various changes, modifications and variations can be made therein without departing from the spirit and scope of the invention as defined in the following claims.

What is claimed is:

1. A peptide or a pharmaceutically acceptable salt thereof, wherein the peptide comprises the amino acid structure of

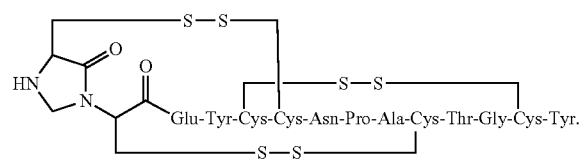

2. The peptide of claim 1, wherein the peptide consists of the amino acid structure of:

3. The peptide of claim 1, wherein the peptide activates the guanylate cyclase C receptor.

4. A pharmaceutical composition comprising a peptide or pharmaceutically acceptable salt thereof according to claim 1.

5. The pharmaceutical composition of claim 4, wherein the pharmaceutical composition further comprises linaclotide.

6. The pharmaceutical composition of claim 4, wherein the pharmaceutical compositions further comprises a peptide comprising an amino acid structure selected from:

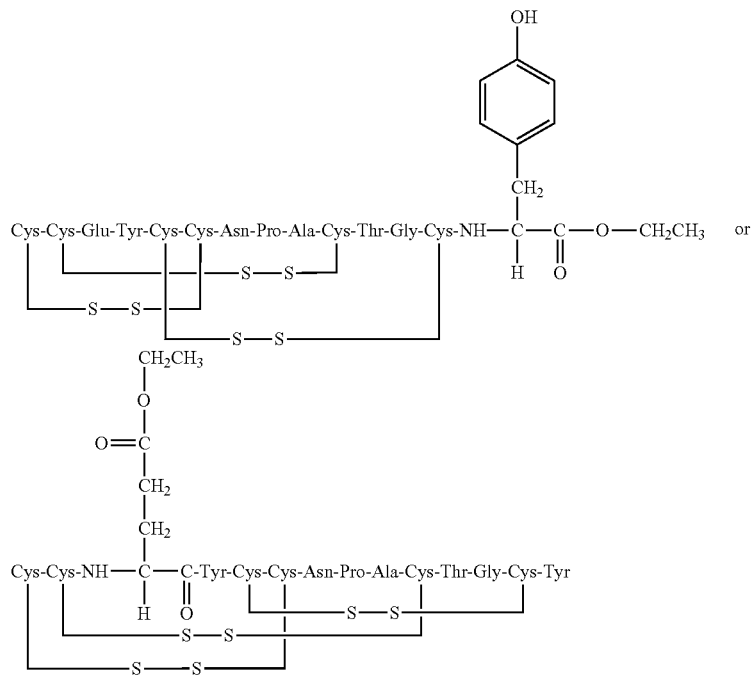

7. The pharmaceutical composition of claim 4, wherein the pharmaceutical composition comprises less than 5% by weight of the peptide or pharmaceutically acceptable salt thereof relative to the total weight of linaclotide.

8. The pharmaceutical composition of claim 7, wherein the pharmaceutical composition comprises less than 4% by weight of the peptide or pharmaceutically acceptable salt thereof relative to the total weight of linaclotide.

9. The pharmaceutical composition of claim 7, further comprising one or more agents selected from (i) a cation selected from $Mg^{2+}$, $Ca^{2+}$, $Zn^{2+}$, $Mn^{2+}$, $K^+$, Na or $Al^{3+}$, or (ii) a sterically hindered primary amine.

10. The pharmaceutical composition of claim 9, wherein said agent is $Mg^{2+}$, $Ca^{2+}$, $Zn^{2+}$, $Mn^{2+}$, $K^+$, $Na^+$ or $Al^{3+}$ is provided as magnesium acetate, magnesium chloride, magnesium phosphate, magnesium sulfate, calcium acetate, calcium chloride, calcium phosphate, calcium sulfate, zinc acetate, zinc chloride, zinc phosphate, zinc sulfate, manganese acetate, manganese chloride, manganese phosphate, manganese sulfate, potassium acetate, potassium chloride, potassium phosphate, potassium sulfate, sodium acetate, sodium chloride, sodium phosphate, sodium sulfate, aluminum acetate, aluminum chloride, aluminum phosphate or aluminum sulfate.

11. The pharmaceutical composition of claim 9, wherein said agent is a sterically hindered primary amine which is an amino acid selected from:
a naturally-occurring amino acid, wherein the naturally-occurring amino acid is histidine, phenylalanine, alanine, glutamic acid, aspartic acid, glutamine, leucine, methionine, asparagine, tyrosine, threonine, isoleucine, tryptophan or valine; or
a non-naturally occurring amino acid or an amino acid derivative, wherein the non-naturally occurring amino acid is 1-aminocyclohexane carboxylic acid, lanthanine or theanine.

12. The pharmaceutical composition of claim 9, wherein the sterically hindered primary amine has the formula:

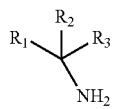

wherein $R_1$, $R_2$ and $R_3$ are independently selected from: H, C(O)OH, C1-C6 alkyl, C1-C6 alkylether, C1-C6 alkylthioether, C1-C6 alkyl carboxylic acid, C1-C6 alkyl carboxylamide and alkylaryl, wherein any group can be singly or multiply substituted with: halogen or amino, and provided that no more than one of $R_1$, $R_2$ and $R_3$ is H.

13. The pharmaceutical composition of claim 12, wherein said pharmaceutical composition further comprises $Mg^{2+}$, $Ca^{2+}$, $Zn^{2+}$, $Mn^{2+}$, $K^+$, $Na^+$ or $Al^{3+}$.

14. The pharmaceutical composition of claim 9, further comprising one or more of
a pharmaceutically acceptable binder or additive, wherein the pharmaceutically acceptable binder or additive is selected from polyvinyl alcohol, polyvinylpyrrolidone (povidone), a starch, maltodextrin or a cellulose ether, wherein the cellulose ether is selected from: methylcellulose, ethylcellulose, carboxymethylcellulose, hydroxyethyl cellulose, hydroxyethyl methylcellulose, hydroxypropyl cellulose and hydroxypropyl methylcellulose;
an antioxidant, wherein said antioxidant is BHA, vitamin E or propyl gallate; or
a pharmaceutically acceptable filler, wherein the pharmaceutically acceptable filler is cellulose, microfine cellulose, microcrystalline cellulose, isomalt, mannitol or dibasic calcium phosphate.

15. A method for treating a gastrointestinal disorder comprising administering the pharmaceutical composition according to claim 7, wherein the gastrointestinal disorder is selected from the group consisting of: irritable bowel syndrome (IBS); constipation-predominant irritable bowel syndrome (c-IBS); constipation; chronic constipation; idiopathic constipation: constipation due to post-operative ileus; constipation caused by opiate use; and visceral pain.

16. The pharmaceutical composition of claim 9 comprising:
i $Ca^{2+}$;
ii leucine;
iii linaclotide; and
iv one or more peptides or pharmaceutically acceptable salt thereof, wherein the peptide comprises an amino acid structure selected from:

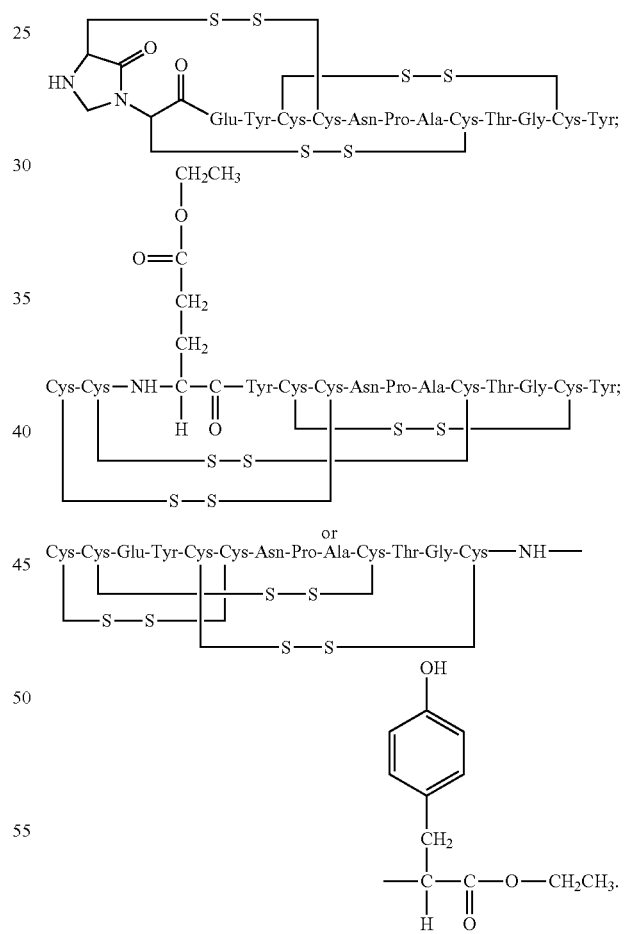

17. The pharmaceutical composition of claim 14, wherein the pharmaceutically acceptable binder is hydroxypropyl methylcellulose and the pharmaceutically acceptable filler is microcrystalline cellulose.

18. The pharmaceutical composition of claim 7, wherein the pharmaceutical composition further comprises a peptide comprising an amino acid structure selected from:

43
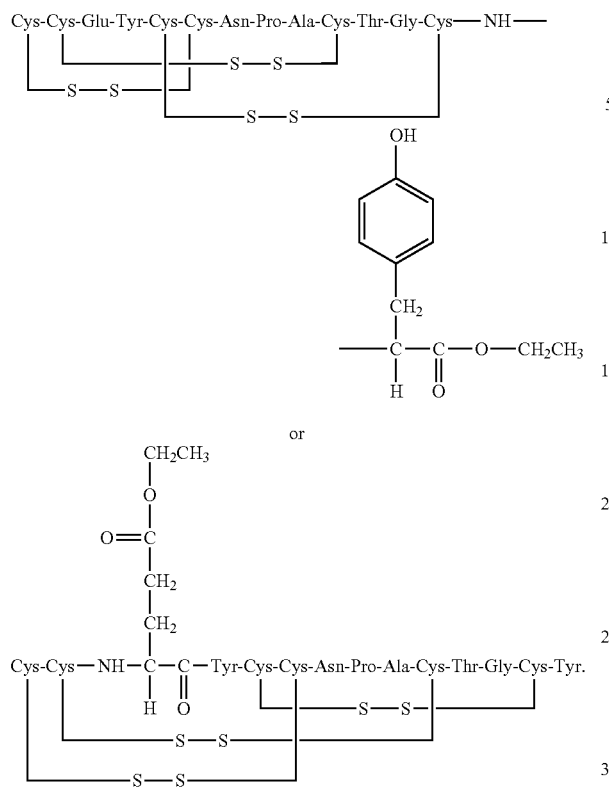
19. The pharmaceutical composition of claim 8, wherein the pharmaceutical composition further comprises a peptide comprising an amino acid structure selected from:
44
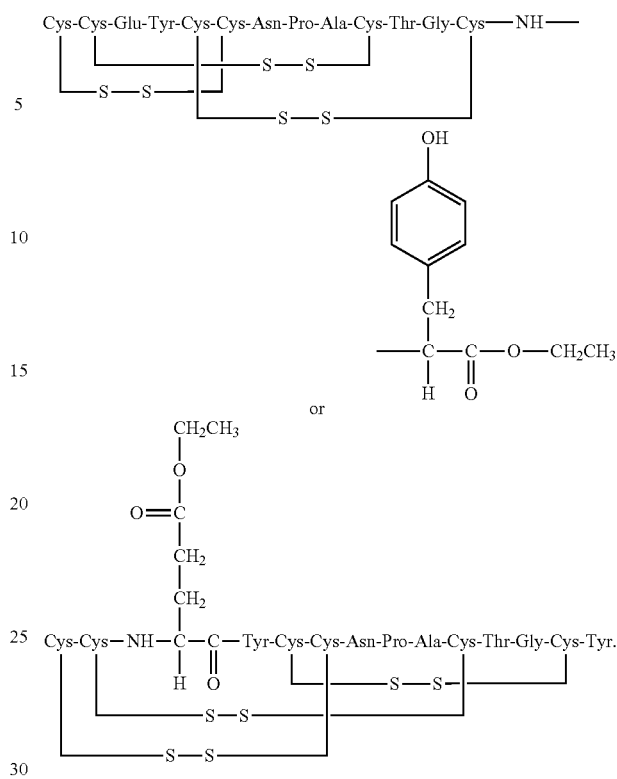
20. The pharmaceutical composition of claim 16, wherein $Ca^{2+}$ is provided as calcium acetate, calcium chloride, calcium phosphate, or calcium sulfate.
* * * * *

UNITED STATES PATENT AND TRADEMARK OFFICE
CERTIFICATE OF CORRECTION

| | | |
|---|---|---|
| PATENT NO. | : 8,933,030 B2 | Page 1 of 1 |
| APPLICATION NO. | : 13/579685 | |
| DATED | : January 13, 2015 | |
| INVENTOR(S) | : Angelika Fretzen et al. | |

It is certified that error appears in the above-identified patent and that said Letters Patent is hereby corrected as shown below:

In the Claims,

Claim 6, column 40, line 32 and claim 7, column 41, line 1, for the claim reference numeral "4", each occurrence, should read --5--.

Signed and Sealed this
Fourth Day of August, 2015

Michelle K. Lee
*Director of the United States Patent and Trademark Office*

SEQUENCE LISTING

<160> NUMBER OF SEQ ID NOS: 1

<210> SEQ ID NO 1
<211> LENGTH: 14
<212> TYPE: PRT

```
<213> ORGANISM: Artificial Sequence
<220> FEATURE:
<223> OTHER INFORMATION: Synthetically generated peptide

<400> SEQUENCE: 1

Cys Cys Glu Tyr Cys Cys Asn Pro Ala Cys Thr Gly Cys Tyr
1               5                   10
```